US012617745B2

(12) United States Patent
Dai et al.

(10) Patent No.: US 12,617,745 B2
(45) Date of Patent: May 5, 2026

(54) CURCUSONE DITERPENOIDS AND USES THEREOF

(71) Applicants: Purdue Research Foundation, West Lafayette, IN (US); University of Florida Research Foundation, Incorporated, Gainesville, FL (US)

(72) Inventors: Mingji Dai, West Lafayette, IN (US); Chengsen Cui, West Lafayette, IN (US); Zhongjian Cai, Jiangsu (CN); Alexander Adibekian, Palm City, FL (US); Brendan Dwyer, Palm Beach Gardens, FL (US)

(73) Assignees: Purdue Research Foundation, West Lafayette, IN (US); University of Florida Research Foundation, Incorporated, Gainesville, FL (US)

( * ) Notice: Subject to any disclaimer, the term of this patent is extended or adjusted under 35 U.S.C. 154(b) by 359 days.

(21) Appl. No.: 18/445,087

(22) PCT Filed: Sep. 27, 2021

(86) PCT No.: PCT/US2021/052148

§ 371 (c)(1),
(2) Date: Mar. 29, 2023

(87) PCT Pub. No.: WO2022/072266

PCT Pub. Date: Apr. 7, 2022

(65) Prior Publication Data

US 2023/0250042 A1 Aug. 10, 2023

Related U.S. Application Data

(60) Provisional application No. 63/084,594, filed on Sep. 29, 2020.

(51) Int. Cl.

| | |
|---|---|
| ***C07C 49/643*** | (2006.01) |
| ***C07C 45/63*** | (2006.01) |
| ***C07C 229/12*** | (2006.01) |
| ***C07D 265/30*** | (2006.01) |

(52) U.S. Cl.
CPC ............ *C07C 49/643* (2013.01); *C07C 45/63* (2013.01); *C07C 229/12* (2013.01); *C07D 265/30* (2013.01)

(58) Field of Classification Search
CPC ..... C07C 49/643; C07C 45/63; C07C 229/12; C07D 265/30
See application file for complete search history.

(56) References Cited

U.S. PATENT DOCUMENTS 5,705,704 A * 1/1998 Brion .................... C07C 49/755
558/287

FOREIGN PATENT DOCUMENTS

| | | |
|---|---|---|
| CN | 116669713 | 8/2023 |
| JP | 2017515491 A | 6/2017 |
| JP | 2023549023 | 11/2023 |
| WO | 2015176749 | 11/2015 |
| WO | 2018236995 | 12/2018 |

OTHER PUBLICATIONS

Li et al. One-Step Semisynthesis Method of Spirocuracasone and Pyracurcasone from Curcusones A and B. Organic Letters, vol. 16, 2196-2199. (Year: 2014).*

Zhang et al. Antitumor Activity of Diterpenoids from Jatropha gossypiifolia: Cell Cycle Arrest and Apoptosis-Inducing Activity in RKO Colon Cancer Cells. Journal of Natural Products, vol. 81, 1701-1710. (Year: 2018).*

Wright et al. Progress toward the Enantioselective Synthesis of Curcusones A-D via a Divinylcyclopropane Rearrangement Strategy. Organic Letters, vol. 21, 9658-9662. (Year: 2019).*

"International Application Serial No. PCT US2021 052148, International Preliminary Report on Patentability mailed Apr. 13, 2023", 6 pgs.

"Substance Record for SID 363899392", Pubchem, [Online]. Retrieved from the Internet: https: pubchem.ncbi.nlm.nih.gov substance 363899392, (May 14, 2018).

"International Application Serial No. PCT US2021 052148, International Search Report mailed Feb. 3, 2022", 4 pgs.

"International Application Serial No. PCT US2021 052148, Written Opinion mailed Feb. 3, 2022", 4 pgs.

Cui, "Total Synthesis and Target Identification of the Curcusone Diterpenes", Journal of the American Chemical Society, vol. 143, No. 11, [Online]. Retrieved from the Internet: URL:https: pubs.acs. org doi 10.1021 jacs.1c00557, (Mar. 11, 2021).

"European Application Serial No. 21876254.0, Extended European Search Report mailed Oct. 23, 2024", 8 pgs.

"Chinese Application Serial No. 202180079302.0, Office Action mailed Oct. 30, 2024", w Machine English translation, 3 pgs.

"Chinese Application Serial No. 202180079302.0, Response filed Nov. 22, 2024 to Office Action mailed Oct. 30, 2024", w English claims (not amended), 8 pgs.

"Chinese Application Serial No. 202180079302.0, Office Action mailed Dec. 11, 2024", w English translation, 26 pgs.

(Continued)

*Primary Examiner* — Sikarl A Witherspoon
(74) *Attorney, Agent, or Firm* — Schwegman Lundberg & Woessner, P.A.

(57) ABSTRACT

The present disclosure provides the first asymmetric total synthesis and target identification of the curcusone natural products. The novel convergent synthesis is built upon a cheap and abundant chiral pool molecule (8) and features a thermal [3,3]-sigmatropic rearrangement and an FeCl3-promoted global hydrolysis/adol condensation cascade to rapidly construct the critical cycloheptadienone core. By performing chemoproteomics with the alkyne probe 37, we identified the previously "undruggable" oncogenic protein BRAT1 as a key cellular target of 1d. Furthermore, 1d inhibits BRAT1 in cancer cells, thereby reducing cancer cell migration, increasing susceptibility to DNA damage, and inducing chemosensitization to the approved drug etoposide. Compound 1d is the first known small-molecule inhibitor for BRAT1, a master regulator of the DDR and DNA repair. Composition matters and methods of uses are within the scope of this disclosure.

17 Claims, 6 Drawing Sheets

(56) References Cited

OTHER PUBLICATIONS

"American Chemical Society, database search result", STN Registry, (Oct. 18, 2018), 7 pgs.
Jie-Qing, Liu, "Cytotoxicity of naturally occurring rhamnofolane diterpenes from Jatropha curcas", Phytochemistry, vol. 96, (Sep. 27, 2013), 1-3.
Ouchi, Toru, "The Potential Role of BRCA1-Associated ATM Activator-1 (BRAT1) in Regulation of mTOR", (Jul. 3, 2013), 3 pgs.
Wang, Hui, "Effects of doxorubicin on the expressions of BRCA1 and PARP-1 proteins in breast cancer MCF-7 cells", TUMOR vol. 33, May 2013, (May 25, 2013), 15 pgs.
"Canadian Application Serial No. 3,194,116, Office Action mailed Feb. 28, 2025", 5 pgs.
"Chinese Application Serial No. 202180079302.0, Office Action mailed Jul. 30, 2025", W/English Translation, 19 pgs.
"Chinese Application Serial No. 202180079302.0, Response filed Apr. 11, 2025 to Office Action mailed Dec. 11, 2024", w/English claims, 19 pgs.
"European Application Serial No. 21876254.0, Response filed May 12, 2025 to Extended European Search Report mailed Oct. 23, 2024", 24 pgs.
"Japanese Application Serial No. 2023-519429, Notification of Reasons for Rejection mailed Sep. 1, 2025", W/English Translation, 7 pgs.
Eui, Young, et al., "The Potential Role of BRCA1-Associated ATM Activator-1 (BRAT 1) in Regulation of mTOR", Journal of cancer biology & research, vol. 1, No. 1, (Jul. 3, 2013), 5 pgs.
Hu, Qingfu, et al., "Effect of triptolide on expression of BRCA1 in triple-negative breast cancer cells", Chinese Journal of Public Health, 34, 07 W/ English Abstract Only, <https://www.zgggws.com/article/doi/10.11847/zgggws1117335>, (Feb. 28, 2018), 3 pgs.
"Chinese Application Serial No. 202180079302.0, Decision of Rejection mailed Jan. 16, 2026", w English translation, 20 pgs.

* cited by examiner

Curcusone D (1d)

37

38

39

40

41 (22%)

42 (42%)

43 (15%)

CURCUSONE DITERPENOIDS AND USES THEREOF

CROSS-REFERENCE TO RELATED APPLICATION

This application is a U.S. national stage filing under 35 U.S.C. 371 from International Application No. PCT/US2021/052148, filed on 27 Sep. 2021, and published as WO 2022/072266 A1 on 7 Apr. 2022, which claims priority to U.S. Provisional Application No. 63/084,594 filed on 29 Sep. 2020, the entirety of which are incorporated herein by reference.

GOVERNMENT RIGHTS

This invention was made with government support under CA023168 and GM128570 awarded by the National Institutes of Health (NIH). The government has certain rights in the invention.

TECHNICAL FIELD

The present disclosure relates to novel curcusone diterpenoid analogs, to novel synthesis of curcusone diterpenoids and analogs, and to methods of using the curcusone diterpenoids and analogs.

BACKGROUND

This section introduces aspects that may help facilitate a better understanding of the disclosure. Accordingly, these statements are to be read in this light and are not to be understood as admissions about what is or is not prior art.

Natural products have been valuable sources and inspirations of lifesaving drug molecules. Their accumulated evolutionary wisdom together with their structural complexity, novelty, and diversity makes them unparalleled for novel therapeutic development. Additionally, natural products can serve as important probe molecules for the elucidation of fundamental biological pathways and identification of novel disease targets. However, their natural scarcity and structural complexity often hamper comprehensive biological evaluations and the elucidation of their mechanisms of action. The latter is also considered as a major bottleneck for natural product-based drug discovery. To overcome these obstacles, total synthesis can be employed to supply key materials and analogs. Meanwhile, many attractive and biologically validated disease targets, especially in cancer, are considered as “undruggable” from a chemical standpoint due to the lack of enzymatic activity and/or small molecule binding sites. The BRCA1-associated ATM activator 1 (BRAT1) protein has been validated as an oncogenic protein but belongs to the “undruggable” category and no small-molecule inhibitor has been identified to target BRAT1.

Therefore, collaborative efforts in the total synthesis and chemoproteomics profiling of curcusone natural products are still needed.

SUMMARY

The present disclosure relates to novel curcusone diterpenoid analogs, to novel synthesis of curcusone diterpenoids and analogs, and to methods of using the curcusone diterpenoids and analogs.

In one embodiment, the present disclosure provides a compound of formula I:

I

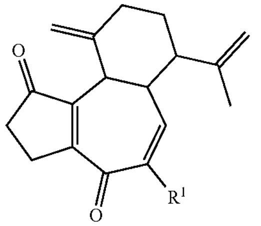

or any stereoisomer, wherein $R^1$ is H, F, Cl, Br, I, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof.

In another embodiment, the present disclosure provides a synthetic method to prepare a curcusone compounds A, B, C, and D or an isomer thereof, wherein the method comprises:

providing a compound of Formula A and treating the compound of Formula A under a halogenation condition to provide a compound of Formula B;

treating the compound of Formula B under a first methylation condition to provide a compound of Formula C, or any isomer thereof; and treating the compound of Formula C under a second methylation condition to provide a compound of Formula D or an isomer thereof, wherein X is Cl, Br, or I.

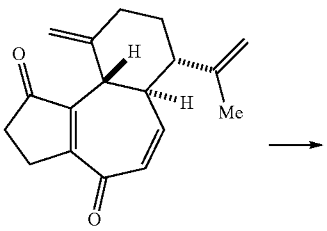

A

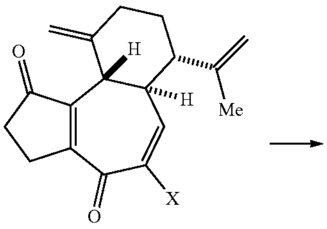

B

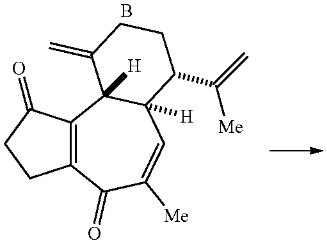

C

-continued

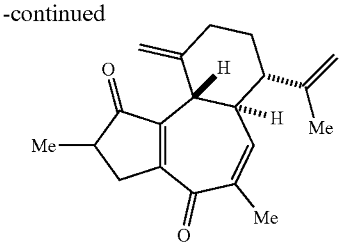

D

DETAILED DESCRIPTION

Figure 1:
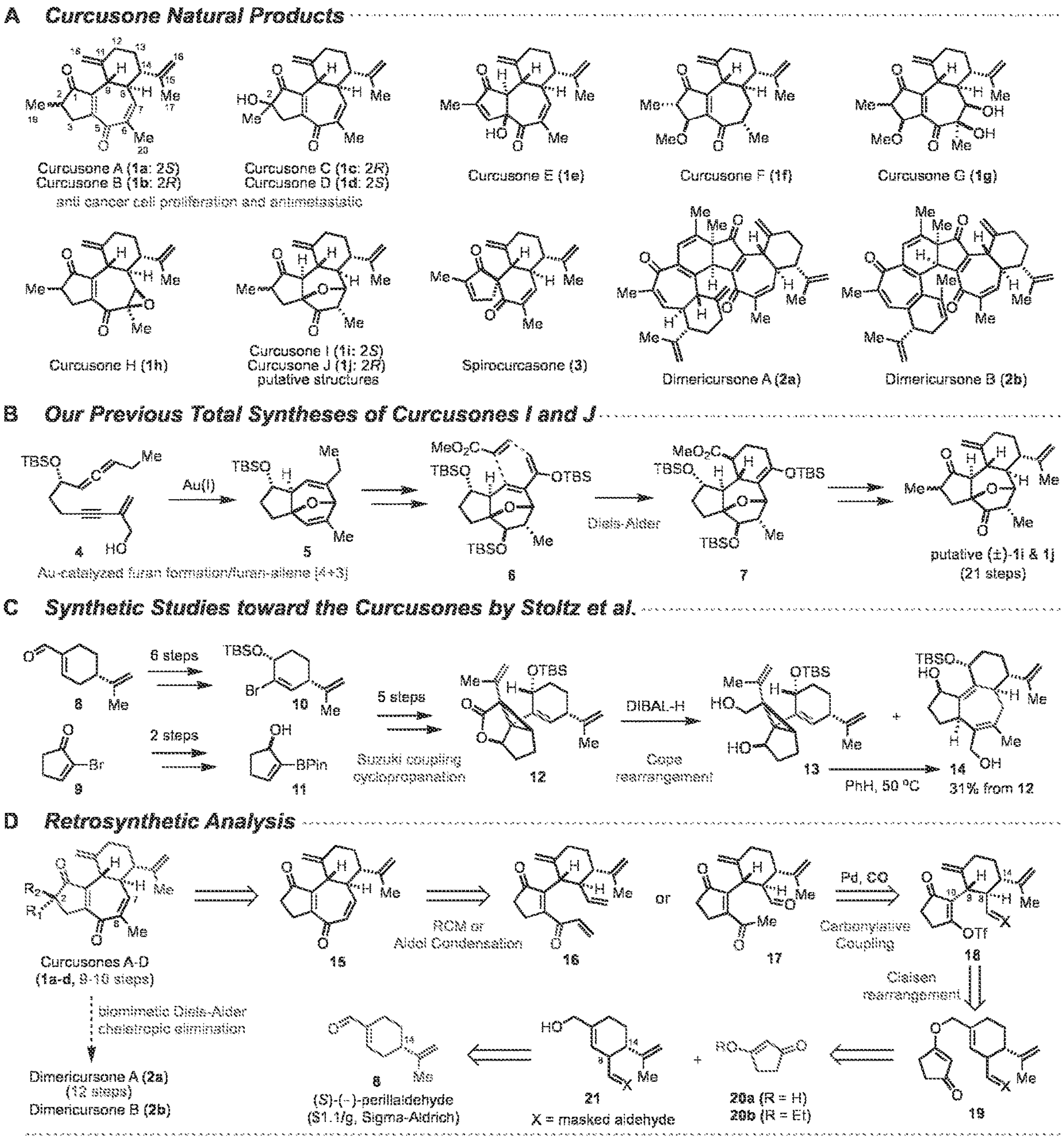
FIG. 1 illustrates curcusone diterpenes and their synthesis.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, $(CH_2)_{0-2}P(O)OR_2$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)C(O)OR$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

Currently, accessing sufficient quantities of natural products such as curcusone diterpene natural products and their analogs for comprehensive biological investigation and therapeutic development remains a significant challenge and hampers studies on their mode of action. Herein, we report a collaborative effort in the total synthesis and target identification of the curcusone natural products which yielded the first total synthesis of curcusones A and B in 9 steps, C and D in 10 steps, and dimericursone A in 12 steps and revealed BRAT1 as a key cellular target of the curcusones.

The curcusone diterpenes (FIG. 1A) were isolated from *Jatropha curcas*, a widely used ingredient in traditional remedies for a variety of ailments including cancer. Structurally, they share a characteristic [6-7-5] tricyclic carbon skeleton with the daphnane and tigliane diterpenes. Curcusones A-D (1a-d), isolated by Clardy and co-workers in 1986, were unambiguously identified as two epimeric pairs at the C2 position. Since then, around thirty curcusone molecules have been isolated including curcusones F-J, which lack the dienone moiety in the seven-membered ring. Structurally rearranged analogs like spirocurcasone (3) and dimeric analogs such as dimericursone A (2a) and dimericursone B (2b) were discovered recently. Among them, curcusones A-D (1a-1d) exhibited low micromolar $IC_{50}$ values against a broad spectrum of human cancer cell lines. However, no total syntheses of curcusones A-D (1a-1d) and their dimeric products (2a and 2b) were reported prior to this study and their mode of action remained unknown.

While the closely related daphnane and tigliane diterpenes have attracted a significant amount of synthetic interest, the curcusone molecules have surprisingly received little attention despite their therapeutic potential. In 2017, we reported the first total syntheses of the putative structures of curcusones I and J (1i and 1j) in 21 steps (FIG. 1B), ultimately leading to the conclusion that the originally proposed structures of both 1i and 1j were incorrect. See Li, Y.; Dai, M. Total Syntheses of the Reported Structures of Curcusones I and J through Tandem Gold Catalysis. *Angew. Chem. Int. Ed* 2017, 56, 11624-11627. Our synthesis involves a gold-catalyzed tandem furan formation and furan-allene [4+3] cycloaddition to build the 5,7-fused ring system with an oxa bridge and a Diels-Alder reaction to construct the 6-membered ring. In 2019, Stoltz and co-workers reported their studies toward synthesizing 1a-1d (FIG. 1C). See (a) Lee, C. W.; Taylor, B. L. H.; Petrova, G. P.; Patel, A.; Morokuma, K.; Houk, K. N.; Stoltz, B. M. An Unexpected Ireland-Claisen Rearrangement Cascade During the Synthesis of the Tricyclic Core of Curcusone C: Mechanistic Elucidation by Trial-and-Error and Automatic Artificial Force-Induced Reaction (AFIR) Computations. *J. Am. Chem. Soc.* 2019, 141, 6995-7004. (b) Wright, A. C.; Lee, C. W.; Stoltz, B. M. Progress toward the Enantioselective Synthesis of Curcusones A-D via a Divinylcyclopropane Rearrangement Strategy. *Org. Lett.* 2019, 21, 9658-9662. (c) Wright, A. C.; Stoltz, B. M. Enantioselective construction of the tricyclic core of curcusones A-D via a cross-electrophile coupling approach. *Chem. Sci.* 2019, 10, 10562-10565. Their approach features an elegant divinylcyclopropane-cycloheptadiene rearrangement to forge the 7-membered ring and reached advanced intermediate 14 after 12 steps from 8.

Our ongoing interest in natural products that can covalently modify cellular proteins prompted us to continue pursuing the total synthesis and target identification of curcusones A-D (1a-1d) with an electrophilic cycloheptadienone moiety. This unique structural feature could allow them to form a covalent bond with nucleophilic residues of certain cellular proteins. Previous cytotoxicity studies found that reduction and/or oxidation of the $C_6$-$C_7$ double bond greatly reduced their anticancer activity. As such, an approach allowing variation of the C6 and C7 substituents would be highly desirable. We envisioned 15 as an advanced intermediate (FIG. 1D). α-Halogenation followed by two methylation reactions would lead to 1a and 1b, which could be oxidized to 1c and 1d via α-hydroxylation. A ring closing metathesis (RCM) or an intramolecular aldol condensation was planned to form the 7-membered dienone (16/17→15). Both 16 and 17 could be prepared from vinyl triflate 18 via Pd-catalyzed carbonylative cross couplings. At this stage, disconnection of the C9-C10 bond could break 18 into two simple pieces, but a direct intermolecular C—C bond formation to construct such a bond is challenging. Thus, we opted for a Claisen rearrangement to forge this C—C bond in a stereoselective manner and designed 19 with a masked aldehyde as the Claisen rearrangement precursor. 19 could be assembled from simple building blocks 20a/20b and 21. The latter could be derived from a cheap chiral pool molecule (S)-(−)-perillaldehyde 8.

Results

Figure 2:
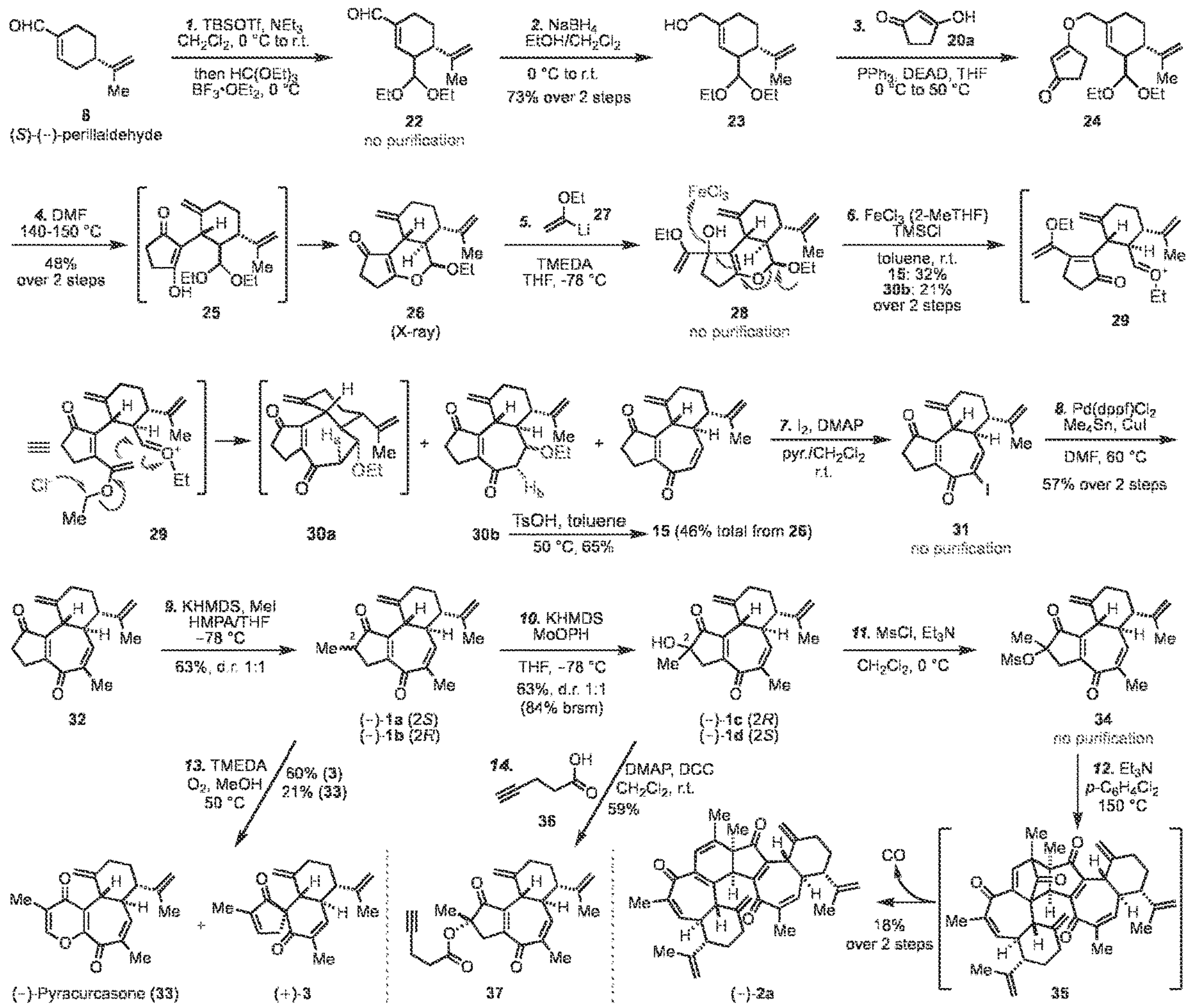
FIG. 2 illustrates total syntheses of curcusones A-D, dimericursone A, and their analogs.

Total Synthesis. Our synthesis started with preparing 23 (FIG. 2), a known compound synthesized from 8 in three steps—extended silyl enol ether formation, vinylogous Mukaiyama aldol reaction, and $NaBH_4$ reduction. We combined the first two steps into a one-pot reaction; crude 22 was then subjected to $NaBH_4$ reduction directly to produce multi-decagram scale of 23 in one batch. We next needed to prepare 24 for the Claisen rearrangement. NaH-promoted addition-elimination between 23 and 20b afforded 24, albeit in low yield (35%). We then used a Mitsunobu reaction between 23 and 20a to prepare 24 but the hydrazine byproduct derived from diethyl azodicarboxylate could not be separated from 24. The recently reported redox-neutral organocatalytic Mitsunobu conditions were also explored but failed to provide 24. Fortunately, the hydrazine byproduct could be tolerated in the Claisen rearrangement. After 24 was heated at 140-150° C. in DMF for 18 h, the Claisen rearrangement did occur, but the rearranged product 25 further cyclized to provide tricyclic compound 26 (CCDC 2033828) as a single diastereomer in 48% yield from 23.

We then decided to continue with 26 and explore the hidden cyclopentane-1,3-dione symmetry to synthesize 17. We started with investigating 1,2-addition of lithiated ethyl vinyl ether (27) to 26 theorizing that a global hydrolysis would release the methyl ketone and the aldehyde at once to form 17 for the aldol condensation. This 1,2-addition turned out to be nontrivial. When two equiv. of 27 was used, only less than 10% yield of 28 was obtained. Owing to their oxophilicity, cerium chloride and lanthanum chloride have been used to promote 1,2-additions. Unfortunately, both failed in our case. Eventually, the 1,2-addition was improved by increasing the amount of 27 to 10 equiv., and 28 was prepared in 57% yield. 28 was then subjected to hydrolysis upon the treatment with TsOH and 17 was obtained in 51% yield from 26. Meanwhile, we were delighted to observe the formation of 15 in the same reaction, albeit in very poor yield (<5%). We were encouraged to achieve a global hydrolysis/aldol condensation cascade to synthesize 15 from 28 in one step and identified $FeCl_3$ in combination with TMSCl as the optimal conditions. When crude 28 was treated with a premixed $FeCl_3$ (0.2 M in 2-methyltetrahydrofuran) and TMSCl in toluene at room temperature, desired product 15 was produced in 32% yield from 26 together with 21% of 30b. The failure of converting 17 to 15 with $FeCl_3$ and the isolation of 30b led us to propose that the $FeCl_3$/TMSCl-promoted cascade process went through intermediates 29 and 30a to form 15 in one step. In intermediate 30a, the α-$H_a$ and the EtO group are anti-periplanar, thus the subsequent 1,2-elimination is facile and occurred under the $FeCl_3$/TMSCl conditions. In intermediate 30b, α-$H_b$ and the EtO group are both in the pseudo equatorial positions, which was supported by NMR analysis and computational modeling. Therefore, its conversion to 15 is more difficult. In order to maximize the overall yield of 15, we investigated conditions to promote the 1,2-elimination of 30b and identified that it could be converted to 15 in 65% yield by heating with TsOH in toluene at 50° C., which brings the overall yield of 15 from 26 to 46%.

With the [6-7-5] tricyclic carbon skeleton quickly assembled in only six steps, we next needed to introduce the two methyl groups. Johnson α-iodination converted 15 to iodoenone 31, which was surprisingly unstable. Therefore, after a quick workup, crude 31 was immediately subjected to the next Stille cross coupling with tetramethylstannane to provide 32 in 57% yield over two steps. Finally, α-methylation of enone 32 at C2 position delivered a 1:1 mixture of separable (−)-curcusone A (1a) and (−)-curcusone B (1b) in 63% yield (9 steps total). α-Hydroxylation of 1a with KHDMS and MoOPH gave separable (−)-curcusone C (1c) and (−)-curcusone D (1d) in 63% yield (d.r. 1:1; 84% brsm; 10 steps total). Additionally, in order to obtain analogs for biological activity comparison, we converted (−)-1b to (+)-spirocurcasone (3) and (−)-33 (a synthetic derivative named as pyracurcasone) by following a reported one-step procedure. The $^{1}H$, $^{13}C$ NMR, and other analytic data of our synthetic samples matched well with the reported ones, which also conclude that the absolute configuration of 1a-1d assigned by Clardy et al. in 1986 is opposite of the actual ones.

We then set out to synthesize dimericursone A (2a) from 1a-1d via a biomimetic dimerization. The proposed biosynthesis of 2a consists of a sequence of oxidative dehydrogenation of 1a/1b or dehydration of 1c/1d to form a reactive cyclopentadienone intermediate followed by Diels-Alder dimerization and cheletropic extrusion of carbon monoxide.[8] From there, 2a could be converted to 2b via another oxidative dehydrogenation and double bond isomerization. We started with 1c and 1d. After an unfruitful attempt to synthesize 2a by heating them directly at elevated temperatures, a 1:1 mixture of them was first converted to their mesylates (34). After extensive exploration, we identified that using triethylamine as a base in 1,4-dichlorobenzene at 150° C. (−)-2a was produced in 18% yield over two steps, which provides direct evidence to support the proposed biosynthetic pathway. Under our conditions, the formation of 2b was not observed.

Probe Synthesis. To elucidate the anticancer mechanism and identify potential cellular targets of curcusones, an alkyne-tagged probe molecule 37 was designed for chemoproteomics studies. Since the dienone is likely protein-reactive and is critical for the observed activity, we decided to minimize structural perturbation of this part and used the tertiary alcohol as a handle to link with a terminal alkyne. 37 was synthesized in 59% yield from (−)-1d via a DCC-promoted coupling with 36.

Figure 3A:
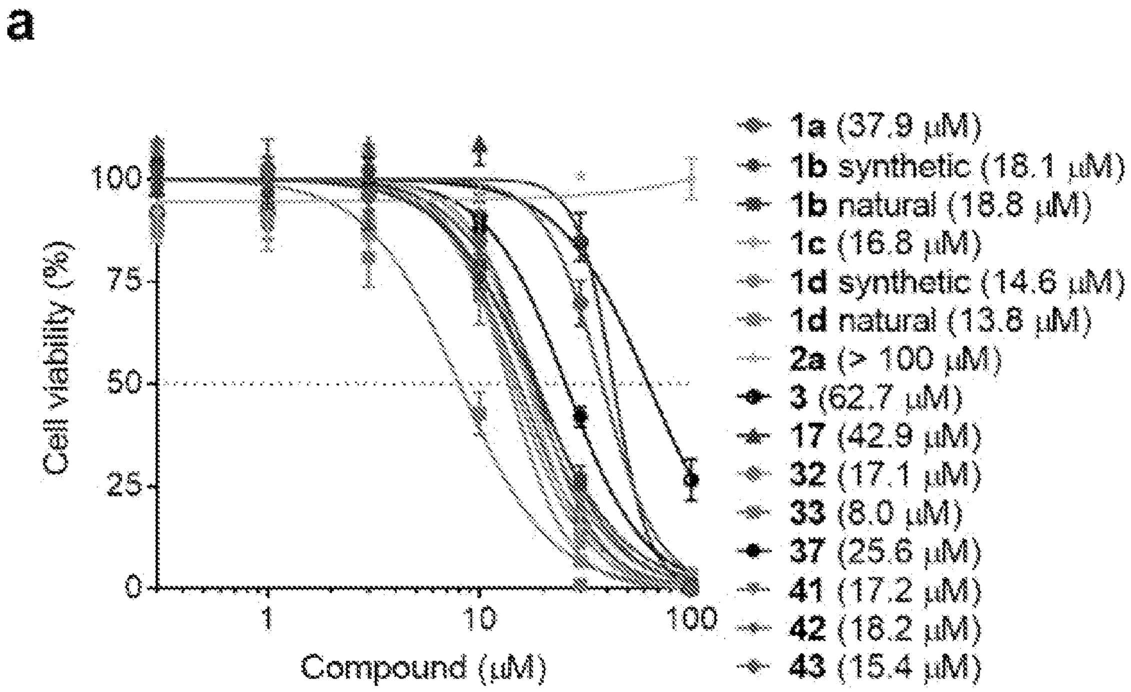
FIG. 3 illustrates identification of BRAT1 as a cellular target of 1d. (A) Viability of MCF-7 cells following 24 h compound treatment with $EC_{50}$ values in brackets (n=3). (B) Scatter plot of proteins competed by 1d from probe 37 (10 μM) enrichment in MCF-7 cells with BRAT1 highlighted (n=3). (C) Western blot (top) and quantification (bottom) of thermal shift assay of overexpressed FLAG-BRAT1 lysate treated with 1d. (D) Western blots of BRAT1 following treatment of live cells with 1d and enrichment by probe 37 in competitive pulldown assays. (E) Western blot (top) and quantification (bottom) of pulldown of BRAT1 with probe 37 in HeLa cells and dose-dependent competition with 1d. All error bars are S.D.

Cytotoxicity and Target Identification. We evaluated the cytotoxicity of curcusones and their analogs in breast cancer MCF-7 cells using the WST-1 assay (FIG. 3A). Synthetic 1a-1d, natural 1b and 1d, and intermediates 15 and 32 exhibited micromolar $EC_{50}$ values against MCF-7 cells with 1d being the most potent curcusone. Importantly, the cytotoxicity values for synthetic 1b and 1d were virtually identical to the values of their naturally isolated counterparts. Analog 33 showed slightly better antiproliferation activity indicating the feasibility of finely tuning the cycloheptadienone moiety to improve potency, but 2a was not active even at 100 μM. Likely due to the full confluency of the tested MCF-7 cells, the $EC_{50}$ values we obtained were about one order of magnitude higher than previously reported (1.6-3.1 μM $EC_{50}$ values for 1a-1d). Gratifyingly, 37 retained similar anticancer properties of 1d, thus warranting its use in competitive chemoproteomic studies.

Figure 3B:
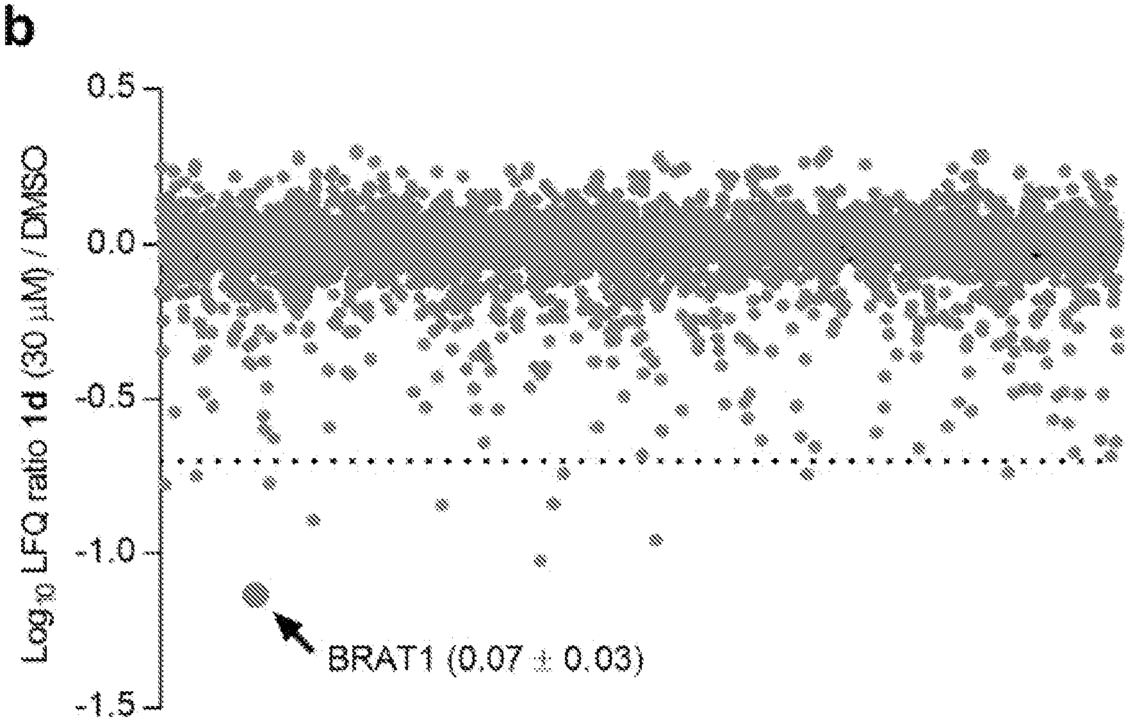

We then identified the cellular targets of curcusones by competitive chemoproteomics using probe 37. MCF-7 cells were treated with 1d or DMSO for 4 hours followed by lysis, treatment with 37, CuAAC with biotin azide, enrichment, digestion, and LC-MS/MS analysis using label-free quantification (FIG. 3B). The best competed target was BRAT1, which acts as a master regulator of the DNA damage response (DDR) and DNA repair by binding to BRCA1 and by activating DDR kinases such as ATM and PRKDC (DNA-PKcs) following DNA damage. Knockdown of BRAT1 increased the constitutive level of apoptosis in human osteosarcoma cells and decreased cancer cell proliferation and tumorigenicity in vitro and in mouse tumor xenografts. BRAT1 is also an unfavorable prognostic marker in kidney and liver cancers. Therefore, targeting BRAT1 is a promising strategy for cancer treatment.

Figure 3C:
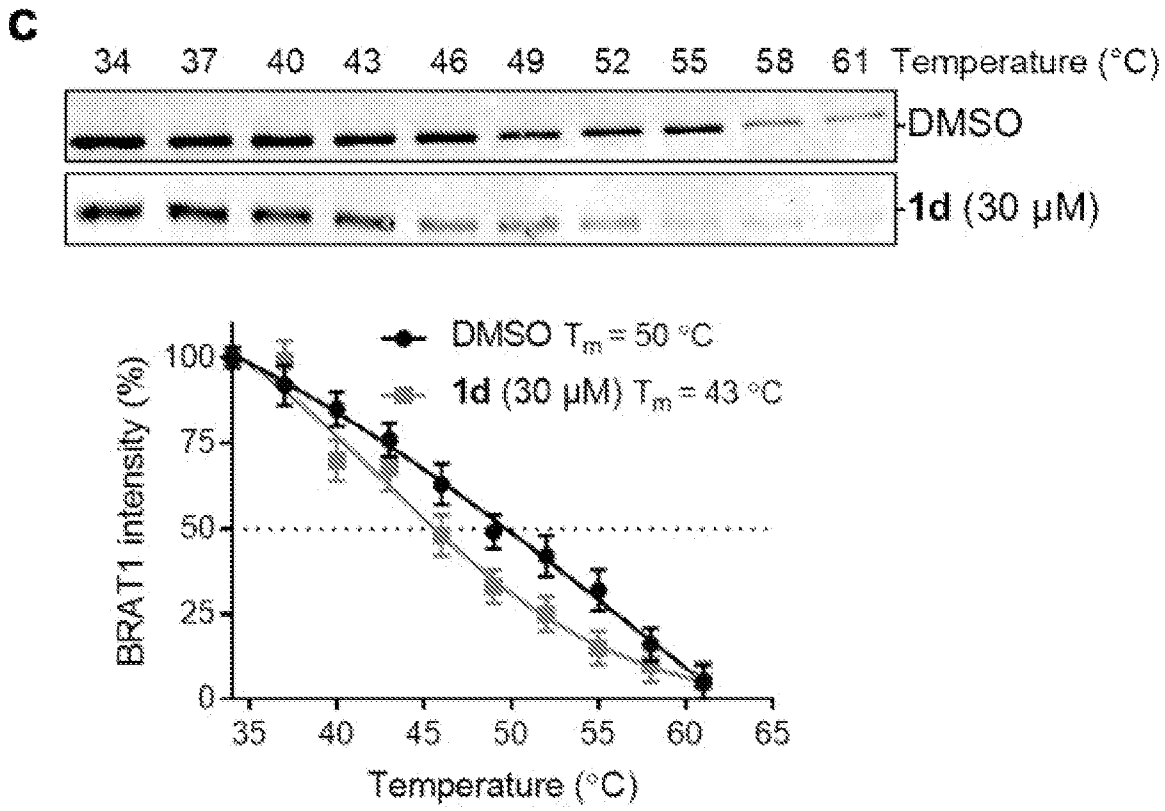
Figure 3D:
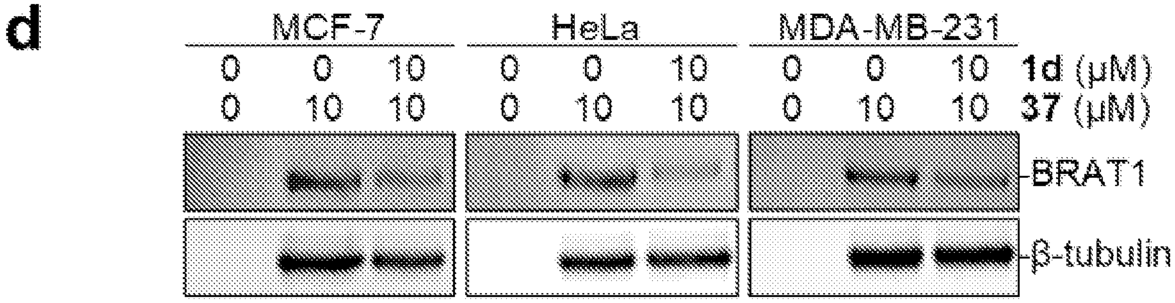
Figure 3E:
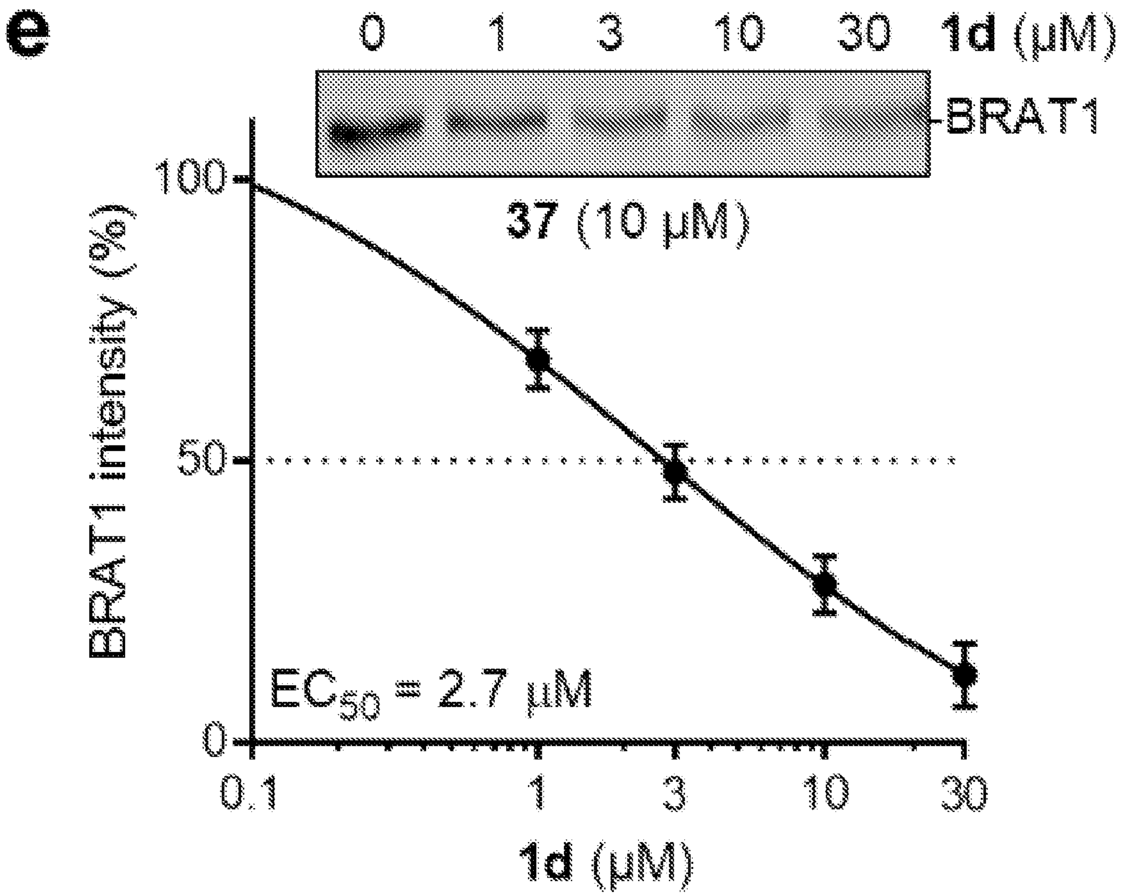
Figure 4:
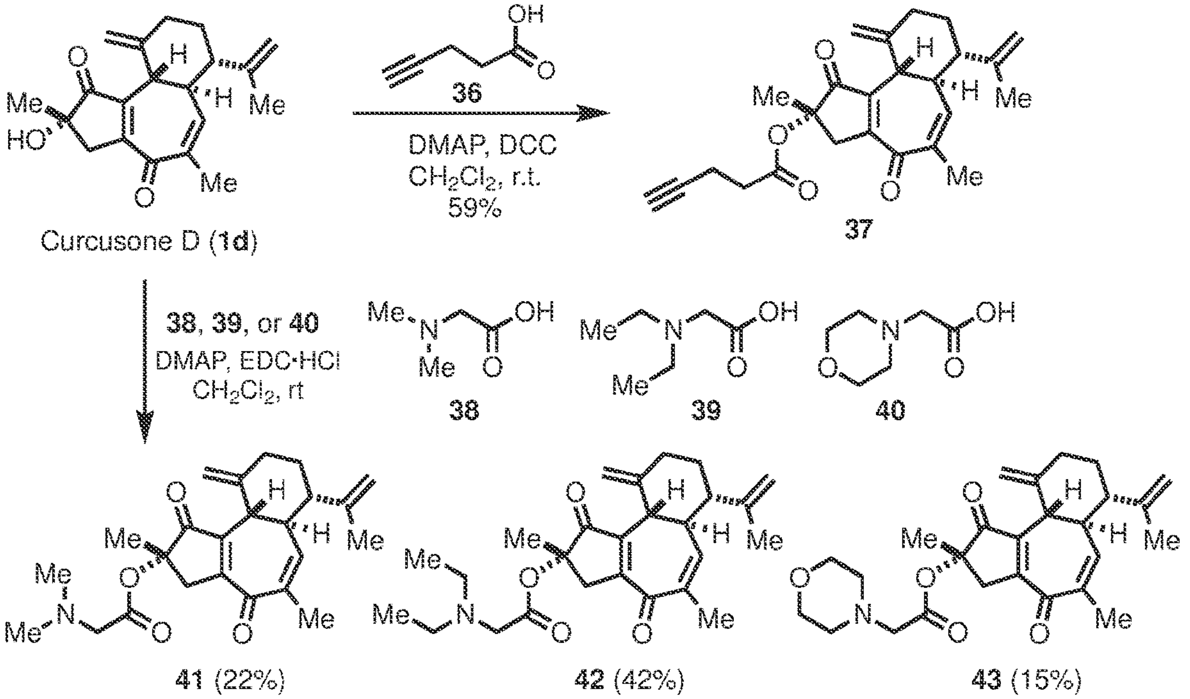
FIG. 4 illustrates syntheses of additional curcusones analogs 41-43.

We next characterized the physical interaction between 1d and BRAT1. We overexpressed FLAG-BRAT1 in HEK-293T cells and performed a thermal shift assay by treating lysates with 1d, heating as indicated, and probing the remaining soluble FLAG-BRAT1 by Western blotting (FIG. 3C). We observed thermal destabilization of 1d-treated BRAT1 indicating a direct interaction. To validate endogenous BRAT1 as a target of 1d in live cells, we employed a competitive pulldown experiment. MCF-7 cells were treated with 1d or DMSO for 4 hours before lysis, treatment with probe 37, CuAAC with biotin azide, streptavidin enrichment, elution, and Western blot visualization. Indeed, native BRAT1 was enriched by 37 and was competed by 1d (FIG. 3D). Additionally, 1d competed the enrichment of BRAT1 from cervical cancer HeLa and triple negative breast cancer MDA-MB-231 cells, thus validating native BRAT1 as a cellular target of 1d across these cell lines. In situ treatment of 1d in live HeLa cells competed BRAT1 enrichment by 37 at low micromolar concentrations ($EC_{50}$=2.7 μM; FIG. 4E). To evaluate the binding reversibility, we performed a competitive BRAT1 pulldown assay with the irreversible cysteine-reactive probe iodoacetamide (IAA). HeLa lysate was treated with 37 (10 μM) for 1 h with either pre- or post-treatment with IAA (30 mM) for 1 h followed by enrichment and Western blot analysis as described above. Indeed, both pre- and posttreatment with IAA competed BRAT1 enrichment by 37, indicating that the curcusone probe forms a covalent bond with a cysteine in BRAT1 and this bond is reversible. We further treated live HeLa cells with different concentrations of 1d for 4 h to evaluate BRAT1 target occupancy via our competitive pulldown assay, which revealed that 1d reaches 50% fractional occupancy (f occ. (50)) at 2.7 μM concentration (FIG. 3E). Collectively, these results demonstrate that 1d is the first small-molecule binder of BRAT1.

BRAT1 Modulation. To determine whether 1d inhibits BRAT1 in cells, we generated stable BRAT1 KD HeLa cells via shRNA retroviral transduction. We then compared the protein expression profiles of BRAT1 KD cells versus 1d-treated cells (3 μM, 24 h) by global proteomics analysis. Among 3347 quantified proteins in compound-treated cells, we found only 36 up- and 42 down-regulated proteins. Importantly, 31 of the 78 dysregulated proteins were also dysregulated in BRAT1 KD cells, thus indicating that 1d functionally inhibits BRAT1 in cells. Notably, several well-known cancer migration and progression drivers were down-regulated, including TRIM47 which mediates cancer migration, the bona fide oncoprotein and potential biomarker WBP2, and frequently highly amplified oncogene FNDC3B. None of these proteins have previously been functionally linked to BRAT1. We then investigated the effect of 1d treatment and BRAT1 KD on cancer cell migration in WT and BRAT1 KD HeLa cells, as well as WT MCF-7 and MDA-MB-231 cells. As expected, BRAT1 knockdown greatly diminished migration of HeLa cells, and treatment with 1d at 1 μM concentration also reduced migration of all cell lines by ~4-fold.

Our global proteomics experiment also revealed several commonly downregulated key DNA repair proteins such as (i) POLD1 which synthesizes DNA during repair, (ii) USP47 which facilitates base-excision repair, (iii) FANCI which mediates the repair of DNA double strand breaks and interstrand crosslinks, and (iv) BRCC3 which stabilizes the accumulation of BRCA1 at DNA breaks. These proteins have not been previously linked to BRAT1 either. Most notably, 1d treatment (24 hours) significantly downregulated the actual physical target, BRAT1 (ratio 0.18), as confirmed by Western blotting. To evaluate whether this effect is due to proteasomal degradation or altered gene expression, we added the proteasome inhibitor MG132 for the final 4 hours of 1d treatment, which recovered BRAT1 protein levels. In contrast, when we measured BRAT1 mRNA levels by RT-qPCR following 1d treatment for 24 hours, we found no difference. Collectively, these findings demonstrate the importance of BRAT1 as a master regulator of the DDR and that 1d inhibition of BRAT1 in cells induces proteasomal degradation over time.

We then investigated whether 1d would potentiate the DNA damaging effect of the clinical drug and topoisomerase inhibitor etoposide via BRAT1 inhibition. WT or BRAT1 KD HeLa cells were treated with DMSO, etoposide, 1d, or etoposide and 1d combined. Subsequent DNA damage was then measured by fluorescence microscopy using γH2AX staining. Treatment with 1d (3 μM) or KD of BRAT1 alone did not increase γH2AX signal. However, co-treatment of 1d with etoposide led to a 2-fold increase. Similarly, etoposide treatment significantly increased γH2AX signal in BRAT1 KD cells, recapitulating the 1d/etoposide co-treatment results. Importantly, 1d treatment did not increase γH2AX signal in etoposide-treated BRAT1 KD cells, confirming that the 1d-etoposide synergism is linked to BRAT1 inactivation. Furthermore, co-treatment of 1d with etoposide also increased cytotoxicity in HeLa, MCF-7, and MDA-MB-231 cells. Likewise, there was increased cell death in BRAT1 KD HeLa cells following etoposide treatment relative to WT cells. Altogether, these results demonstrate that targeting BRAT1 with 1d is a promising anticancer strategy for chemosensitization to DNA damaging drugs.

Analog Synthesis. Three more analogs (41-43) were synthesized from (−)-curcusone D (1d) by coupling with amino acids 38-40 (FIG. 4) These analogs could help validate the notion that the tertiary alcohol position could be modified without significantly changing the curcusones' anticancer activity and provide information to guide future analog design and preparation to improve their druglike properties.

Cancer Cell Proliferation Inhibition. We initiated our biology studies by testing the cytotoxicity of the (−)-curcusones 1a-1d, (−)-dimericurcusone 2a, (+)-spirocurcasone (3), (−)-pyracurcasone (33), and semisynthetic analogs 41-43 as well as two synthetic intermediates (15 and 32) in breast cancer MCF-7 cells. Cells were treated with various concentrations of the compounds for 24 h, and cell viability was measured by imaging the cells and the WST-1 assay (FIG. 4*a*). Possibly due to the full confluency of the tested MCF-7 cells, the $IC_{50}$ values we obtained were about one order of magnitude higher than previously reported (1.6-3.1 μM $IC_{50}$ values for natural 1a-1d). Nonetheless, synthetic curcusones 1a-1d, natural 1b and 1d, as well as the synthetic intermediates 15 and 32 exhibited micromolar $EC_{50}$ values against MCF-7 cells with curcusone D (1d) displaying the strongest cytotoxic effect (13.8 μM) among curcusones. Most importantly, in our hands, the cytotoxicity values for the synthetic curcusones B (1b) and D (1d) were virtually identical to the cytotoxicity values of their naturally isolated counterparts, which rules out the possibility that the $IC_{50}$ value differences between ours and the reported ones were caused by the origin of the sample (synthetic vs. natural). Additionally, the $IC_{50}$ values of spirocurcasone (3) and pyracurcasone (33) were about one order of magnitude higher than the reported ones as well.[21] The high $IC_{50}$ value of 3 (62.7 μM) emphasizes the importance of the cycloheptadienone moiety of the curcusones and the slightly better antiproliferation activity of 33 (8.0 μM) indicates that the cycloheptadienone moiety could be finely tuned to improve potency. Interestingly, the dimericursone A (2a) showed no toxicity in MCF-7 cells. Gratifyingly, our alkyne probe 37 and semisynthetic curcusone analogs 41-43 retained the anticancer properties of the parent molecule 1d, thus warranting the use of 37 as a proteomic probe for curcusone D cellular target discovery.

In summary, we completed the first asymmetric total synthesis and target identification of the curcusone natural products. Our convergent synthesis builds upon a cheap and abundant chiral pool molecule (8) and features a thermal [3,3]-sigmatropic rearrangement and an $FeCl_3$-promoted global hydrolysis/aldol condensation cascade to rapidly construct the critical cycloheptadienone core. This efficient synthetic route yielded curcusones A and B (1a and 1b) in only 9 steps, curcusones C and D (1c and 1d) in 10 steps, and dimericursone A (2a) in 12 steps from (S)-(−)-8. The successful synthesis of 2a from 1e/1d experimentally supports the proposed Diels-Alder dimerization and cheletropic extrusion biosynthesis. By performing chemoproteomics with the alkyne probe 37, we identified the previously "undruggable" oncogenic protein BRAT1 as a key cellular target of 1d. Furthermore, 1d inhibits BRAT1 in cancer cells, thereby reducing cancer cell migration, increasing susceptibility to DNA damage, and inducing chemosensitization to the approved drug etoposide. To our knowledge, 1d is the first known small-molecule inhibitor of BRAT1, a master regulator of the DDR and DNA repair. Many promising clinical trials are underway targeting DDR proteins such as PARP, ATR, ATM, CHK, and DNA-PK as monotherapies or in combination with other treatments. Olaparib, a PARP inhibitor, was approved by FDA in 2014 as a monotherapy to treat germline BRCA1/2-mutant ovarian cancer. Our concise and convergent total synthesis has opened the gate for curcusone analog synthesis and structure-activity optimizations, which may thus yield novel BRAT1 inhibitors as potential lead medicines for monotherapies or combination therapies.

General Methods. NMR spectra were recorded on Bruker spectrometers ($^1H$ at 400 MHz, 500 MHz, 800 MHz and $^{13}C$ at 100 MHz, 125 MHz, 200 MHz). Chemical shifts (δ) were given in ppm with reference to solvent signals [$^1H$ NMR: $CHCl_3$ (7.26); $^{13}C$ NMR: $CDCl_3$ (77.16), $C_6D_6$ (128.02), $CD_3OD$ (49.0)]. Column chromatography was performed on silica gel. All reactions sensitive to air or moisture were conducted under argon atmosphere in dry and freshly distilled solvents under anhydrous conditions, unless otherwise noted. Anhydrous THF and toluene were distilled over sodium benzophenone ketyl under Argon. Anhydrous $CH_2Cl_2$ was distilled over calcium hydride under Argon. All other solvents and reagents were used as obtained from commercial sources without further purification. Room temperature (r.t.) is around 23° C.

Experiment Procedure and Spectra Data

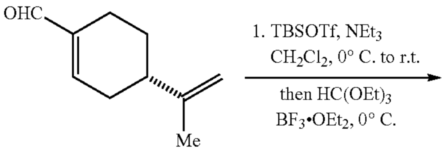

8
(S)-(-)perillaldehyde

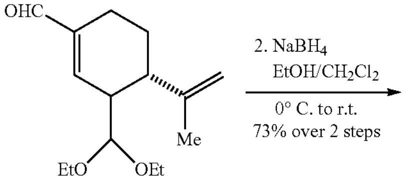

22
no purification

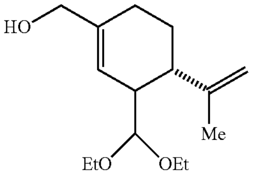

23

To a solution of (S)-(−)-perillaldehyde 8 (7.8 mL, 50 mmol) in $CH_2Cl_2$ (500 mL), triethylamine (10.5 mL, 75.0 mmol) and tert-butyldimethylsilyl trifluoromethanesulfonate (13.8 mL, 60.0 mmol) were added at 0° C. The reaction mixture was warmed to room temperature and stirred for 25 min. The reaction mixture was then cooled to 0° C., followed by addition of triethyl orthoformate (33.3 mL, 200 mmol) and boron trifluoride diethyl etherate (8.0 mL, 65 mmol). The reaction mixture was stirred at 0° C. for 25 min before it was quenched with saturated aqueous sodium bicarbonate (250 mL) and extracted with $CH_2Cl_2$ (2×100 mL). The combined organic layers were dried ($Na_2SO_4$), filtered, and concentrated to provide crude 22, which was used directly in the next step.

The above crude residue 22 was dissolved in a mixture of $CH_2Cl_2$ (500 mL) and EtOH (100 mL). Sodium borohydride (4.73 g, 125 mmol) was added at 0° C. The reaction mixture was vigorously stirred at room temperature for 2 h before it was quenched with water (200 mL) and extracted with $CH_2Cl_2$ (3×100 mL). The combined organic layers were washed with brine (200 mL), dried ($Na_2SO_4$), filtered, and concentrated in vacuo. The residue was purified by column chromatography (hexane/EtOAc=4/1 to 2/1) to give known compound 23 (10.1 g, 73%) as pale-yellow liquid. $^1$H NMR (500 MHz, $CDCl_3$) δ=5.82 (br m, 1H), 4.78 (br m, 1H), 4.74 (br m, 1H), 4.35 (d, J=3.9 Hz, 1H), 4.05-3.98 (br s, 2H), 3.74 (dq, J=9.7, 7.1 Hz, 1H), 3.59 (dq, J=9.2, 7.0 Hz, 1H), 3.49 (dp, J=9.7, 7.0 Hz, 2H), 2.49-2.43 (m, 1H), 2.26 (ddd, J=10.8, 9.1, 3.2 Hz, 1H), 2.11-2.05 (m, 2H), 1.74-1.69 (m, 4H, including s, 3H, at δ=1.72), 1.65-1.57 (m, 2H), 1.21 (t, J=7.0 Hz, 3H), 1.18 (t, J=7.1 Hz, 3H). $^{13}$C NMR (125 MHz, $CDCl_3$) δ=148.0, 138.8, 121.4, 110.9, 104.2, 67.5, 64.2, 63.1, 43.1, 42.3, 27.7, 25.2, 19.9, 15.4, 15.3; $[\alpha]_D^{25}$=+77.0 (c 0.5, $CHCl_3$) [$[\alpha]_D^{27}$=+75.6 (c 1.0, $CHCl_3$)].

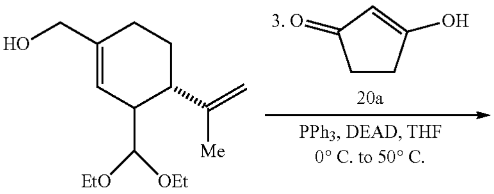

23

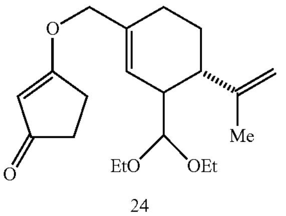

24

To a solution of alcohol 23 (8.44 g, 33.2 mmol) in THF (500 mL), 1,3-cyclopentanedione (7.90 g, 80.5 mmol) and triphenyl phosphine (21.8 g, 83.1 mmol) were added. The reaction mixture was stirred for 5 min at room temperature and then cooled to 0° C. Diethyl azodicarboxylate solution (40% w.t. in toluene, 37.8 mL, 83.0 mmol) was added at 0° C. over a period of 5 min, and the resultant brown solution was immediately placed in a pre-heated oil-bath (50° C.). The reaction mixture was stirred at 50° C. for 25 min and then cooled to room temperature. Removal of THF under reduced pressure afforded a black oil, which was diluted by $Et_2O$ (300 mL) and filtered over Celite. The filtrate was concentrated, and the residue was purified by column chromatography (hexane/EtOAc=10/1 to 2/1) to give an orange solid-liquid mixture. 100 mL hexane was added to this crude product. The mixture was sonicated for 2 min and then filtered. The filtrate was concentrated under reduced pressure to give 24 (10.2 g, containing trace amounts of triphenylphosphine oxide and diethyl 1,2-hydrazinedicarboxylate) as orange liquid, which was directly used in the next step. $^1$H NMR (500 MHz, $CDCl_3$) δ=5.99 (s, 1H), 5.33 (s, 1H), 4.82-4.80 (m, 1H), 4.76-4.74 (m, 1H), 4.41 (s, 2H), 4.37 (d, J=3.7 Hz, 1H), 3.75 (dq, J=9.6, 7.0 Hz, 1H), 3.61 (dq, J=9.3, 7.0 Hz, 1H), 3.54-3.44 (m, 2H), 2.64-2.59 (m, 2H), 2.52-2.47 (m, 1H), 2.45-2.41 (m, 2H), 2.27 (ddd, J=10.3, 9.3, 3.1 Hz, 1H), 2.13-2.07 (m, 2H), 1.78-1.70 (m, 4H, including s, 3H, at δ=1.73), 1.64 (dddd, J=12.8, 10.9, 8.7, 6.9 Hz, 1H), 1.22 (t, J=7.0 Hz, 3H), 1.19 (t, J=7.1 Hz, 3H); $^{13}$C NMR (125 MHz, $CDCl_3$) δ=206.3, 190.3, 147.7, 133.0, 126.9, 111.4, 105.3, 103.9, 76.4, 64.5, 63.4, 42.9, 42.7, 34.1, 28.8, 27.6, 25.4, 19.9, 15.6 15.4; HRMS (ESI): m/z Calc. for $C_{20}H_{30}O_4Na$ $[M+H]^+$: 357.2036, found: 357.2034. IR (film): 2974, 2927, 1702, 1675, 1587, 1439, 1385, 1336, 1247, 1177, 1110, 1090, 1056 $cm^{-1}$; $[\alpha]_D^{23}$=+59.3 (c=0.3, $CHCl_3$).

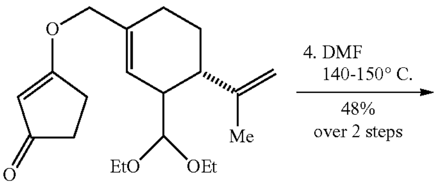

24

-continued

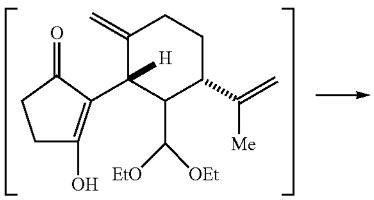

25

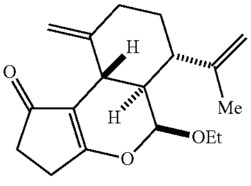

26

A solution of vinylogous ester 24 (10.2 g, 30.5 mmol) in DMF (250 mL) was heated at 140-150° C. for 18 h. Upon completion, the reaction mixture was cooled to room temperature, diluted with $Et_2O$ (500 mL), and washed with saturated aqueous sodium bicarbonate (100 mL) then water (2×100 mL). The combined aqueous layers were further extracted with $Et_2O$ (2×100 mL). The combined organic layers were dried ($Na_2SO_4$), filtered, and concentrated. The residue was purified by column chromatography (hexane/EtOAc=10/1 to 4/1 to 2/1) to give 26 (4.57 g, 48% over 2 steps from 24) as orange solid. $^1H$ NMR (500 MHz, $CDCl_3$) δ=5.07 (d, J=2.2 Hz, 1H), 4.87-4.85 (m, 1H), 4.83-4.81 (m, 1H), 4.81-4.79 (m, 1H), 4.56 (s, 1H), 3.79 (dq, J=9.7, 7.0 Hz, 1H), 3.56 (dq, J=9.7, 7.1 Hz, 1H), 2.99 (d, J=11.5 Hz, 1H), 2.65-2.57 (m, 1H), 2.54-2.35 (m, 5H), 2.24 (td, J=13.1, 4.6 Hz, 1H), 1.84 (dtd, J=12.8, 4.4, 2.4 Hz, 1H), 1.67 (s, 3H), 1.59 (td, J=11.3, 2.3 Hz, 1H), 1.51 (qd, J=12.9, 4.6 Hz, 1H), 1.18 (t, J=7.1 Hz, 3H); $^{13}C$ NMR (125 MHz, $CDCl_3$) δ=202.6, 182.8, 146.1, 145.9, 116.2, 112.5, 107.7, 101.2, 65.4, 46.8, 46.4, 36.4, 35.9, 34.5, 33.6, 26.4, 19.0, 15.2; IR (film): 2976, 2930, 1697, 1627, 1394, 1163, 1076 $cm^{-1}$; HRMS (ESI): m/z Calc. for $C_{18}H_{25}O_3$ $[M+H]^+$: 289.1798, found: 289.1798; $[\alpha]_D^{24}$=−251.6 (c=0.5, $CHCl_3$).

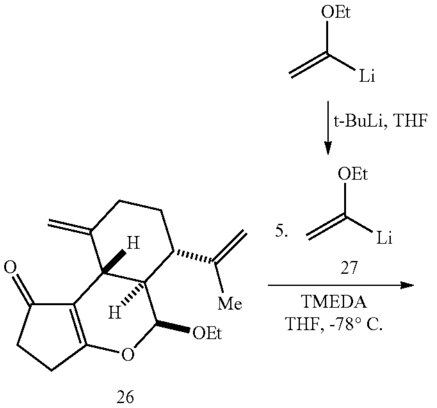

26

-continued

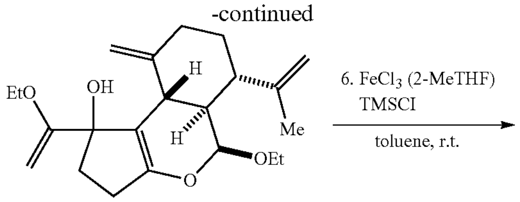

28
no purification

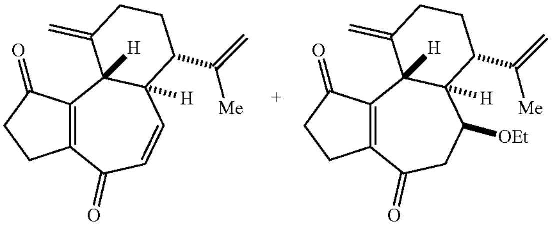

15
32% over 2 steps 30b
21% over 2 steps

To a solution of ethyl vinyl ether (0.64 mL, 6.94 mmol) in anhydrous THF (12 mL) at −78° C. under argon, was added t-BuLi (1.7 M in pentane, 4.2 mL, 6.94 mmol) dropwise. The reaction mixture was stirred at −78° C. for 5 min and then warm up to 0° C. and further stirred for 30 min. The mixture was re-cooled to −78° C. and TMEDA (1.0 mL) was added. After stirred for 30 min, compound 26 (200 mg, 0.69 mmol) in anhydrous THF (2.0 mL) was added slowly. The reaction mixture was stirred at −78° C. for 1 h and then warm up to 0° C. and stirred for 30 min. The reaction was quenched with $H_2O$ (10 mL) and $Et_2O$ (15 mL). The aqueous layer was extracted with $Et_2O$ (5 mL) and the combined organic layers were dried over $Na_2SO_4$, filtered, and concentrated in vacuo. The crude product 28 was used for next step without purification.

$FeCl_3$ (0.2 M in 2-Me-THF, 3.5 mL, 0.69 mmol) and TMSCl (37 mg, 0.35 mmol) was premixed in a reaction flask with toluene (5 mL) at room temperature. Crude compound 28 (prepared above) in toluene (3 mL) was added dropwise slowly to the reaction mixture via a syringe pump in 2 h. The reaction was further stirred at room temperature for 20 h. The reaction mixture was then quenched with $H_2O$ (5 mL) and separated. The aqueous phase was extracted with $Et_2O$ (15 mL). The combined organic phase was washed with brine, dried over $Na_2SO_4$, filtered, and concentrated in vacuo. The crude residue was purified by column chromatography (10% EtOAc in hexane) to give 15 (59 mg, 32% yield over 2 steps from 26) as a white solid and 30b (45 mg, 21% from 26) as a colorless oil.

Compound 15: $^1H$ NMR (500 MHz, $CDCl_3$) δ=6.25 (dd, J=11.8, 4.6 Hz, 1H), 6.11 (dd, J=11.8, 2.3 Hz, 1H), 4.87 (t, J=1.7 Hz, 1H), 4.84 (s, 1H), 4.79 (s, 1H), 4.24 (s, 1H), 3.26 (dt, J=12.3, 3.2 Hz, 1H), 3.02-2.96 (m, 1H), 2.69 (ddd, J=11.8, 4.6, 2.3 Hz, 1H), 2.66-2.60 (m, 1H), 2.48 (dd, J=5.4, 4.5 Hz, 2H), 2.47-2.43 (m, 1H), 2.40 (td, J=11.8, 4.3 Hz, 1H), 2.30 (td, J=12.5, 4.7 Hz, 1H), 1.93-1.88 (m, 1H), 1.61 (s, 3H), 1.50 (ddd, J=12.6, 4.8 Hz, 1H); $^{13}C$ NMR (125 MHz, $CDCl_3$) δ=209.6, 194.8, 160.6, 149.4, 149.1, 146.7, 143.4, 133.3, 113.8, 108.6, 51.4, 46.3, 44.1, 36.4, 34.4, 34.0, 26.7, 18.8; IR (film): 2928, 1713, 1637, 1442, 1376, 1173, 899 $cm^{-1}$; HRMS (ESI): m/z Calc. for $C_{18}H_{21}O_2[M+H]^+$: 269.1536, found: 269.1537; $[\alpha]_D^{25}$=−303 (c=0.2, $CHCl_3$).

Compound 30b: $^1H$ NMR (500 MHz, $CDCl_3$) δ=4.85 (s, 1H), 4.80 (s, 1H), 4.68 (s, 1H), 4.08 (s, 1H), 3.71 (dd, J=3.6, 3.6 Hz, 1H), 3.53-3.47 (m, 1H), 3.38-3.33 (m, 1H), 3.32 (d, J=10.7 Hz, 1H), 3.04-2.96 (m, 2H), 2.68 (dd, J=18.7, 4.1 Hz, 1H), 2.61-2.54 (m, 1H), 2.52-2.45 (m, 3H), 2.42-2.38 (m, 1H), 2.33 (dd, J=12.8, 4.3 Hz, 1H), 1.89-1.86 (m, 1H), 1.78 (t, J=11.0 Hz, 1H), 1.61 (s, 3H), 1.49 (qd, J=13.0, 5.0 Hz, 1H), 1.07 (t, J=6.9 Hz, 3H), $^{13}$C NMR (125 MHz, $CDCl_3$) δ=209.6, 203.0, 160.7, 150.6, 149.0, 113.4, 106.7, 72.8, 65.6, 50.5, 49.7, 49.6, 43.7, 36.4, 34.8, 34.2, 26.6, 19.1, 15.7; IR (film): 2926, 2856, 1713, 1660, 1442, 1377, 1261, 1181, 1089 $cm^{-1}$; HRMS (ESI): m/z Calc. for $C_{20}H_{27}O_3$ $[M+H]^+$: 315.1954. found: 315.1953: $[\alpha]_D^{25}$=−198 (c=0.057, $CHCl_3$).

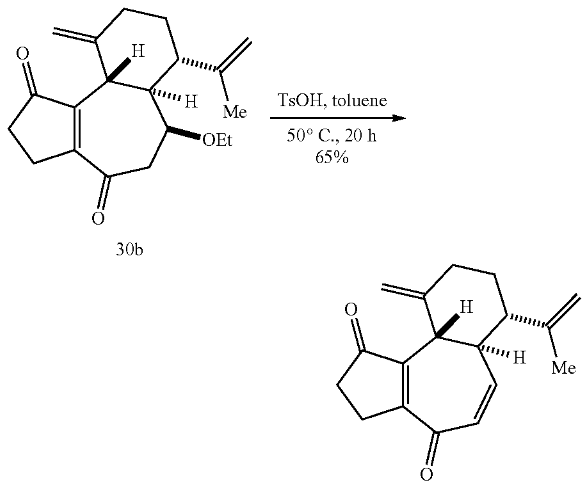

30b

15

A solution of compound 30b (45 mg, 0.14 mmol) and TsOH (2 mg, 0.01 mmol) in toluene (1.5 mL) at δ0° C. stirred for 20 h. The reaction mixture was cool to room temperature and quenched with $H_2O$ (1 mL). The aqueous layer was extracted with $Et_2O$ (5 mL) and the combined organic layer was washed with brine, dried over $Na_2SO_4$, filtered, and concentrated in vacuo. The crude residue was purified by column chromatography ($SiO_2$, 10% EtOAc in hexane to enone 15 (24 mg, 65%) as white solid.

-continued

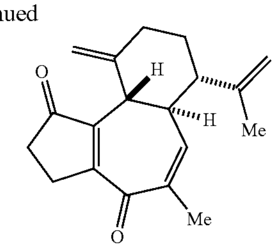

32

To a solution of enone 15 (10 mg, 0.037 mmol) in anhydrous $CH_2Cl_2$/pyridine (2 ml, 5:1) at room temperature was added $I_2$ (28 mg, 0.11 mmol) and DMAP (13.4 mg, 0.11 mmol). The reaction mixture was stirred at room temperature for 5 h before quenching with $H_2O$ (2 mL). The mixture was filtered through Celite and the layers were separated. The organic layer was washed with $H_2O$, brine, dried over $Na_2SO_4$, filtered, and concentrated in vacuo. The crude product 31 was used for next step without purification.

A solution of crude 31 (prepared above) in DMF (2 mL, degassed with argon) at room temperature were added $Pd(dppf)Cl_2$ (3 mg, 0.0034 mmol), CuI (2 mg, 0.01 mmol) and $Me_4Sn$ (2 drops). The reaction mixture was bubbled with argon for 10 min and then put into oil bath (pre-heated at 60° C.). The mixture was stirred at 60° C. for 1 h before cooling to room temperature and then diluted with $Et_2O$ (6 mL) and $H_2O$ (2 mL). The organic layer was washed with $H_2O$ (2 mL), brine (2 mL), dried over $Na_2SO_4$, filtered, and concentrated in vacuo. The crude residue was purified by silica gel column chromatography (10% EtOAc in hexane) to give enone 32 (4.7 mg, 45% over 2 steps from 15) as white solid. $^1$H NMR (500 MHz, $CDCl_3$) δ=5.87 (dq, J=5.2, 1.5 Hz, 1H), 4.84 (s, 1H), 4.82 (s, 1H), 4.76 (s, 1H), 4.20 (s, 1H), 3.15 (d, J=12.3 Hz, 1H), 3.07-3.01 (m, 1H), 2.62-2.25 (m, 2H), 2.48 (d, J=4.20 Hz, 1H), 2.47 (d, J=3.7 Hz, 1H), 2.43 (dddd, J=12.7, 4.4, 2.7, 2.7, Hz, 1H), 2.35 (td, J=11.9, 4.1 Hz, 1H), 2.28 (td, J=12.8, 4.3 Hz, 1H), 1.91-1.86 (m, 1H), 1.85 (t, J=1.5 Hz, 3H), 1.56 (s, 3H), 1.46 (qd, J=12.7, 4.4 Hz, 1H); $^{13}$C NMR (125 MHz, $CDCl_3$) δ=209.9, 198.7, 161.2, 149.3, 148.9, 147.0, 141.0, 136.5, 113.4, 108.4, 51.8, 45.9, 43.8, 36.7, 34.6, 34.0, 27.3, 19.6, 18.8; IR (film): 2930, 2864, 1728, 1646, 1442, 1170 $cm^{-1}$; HRMS (ESI): m/z Calc. for $C_{19}H_{23}O_2$ $[M+H]^+$: 283.1693, found. 283.1693; $[\alpha]_D^{24}$=−418 (c=0.06, $CHCl_3$).

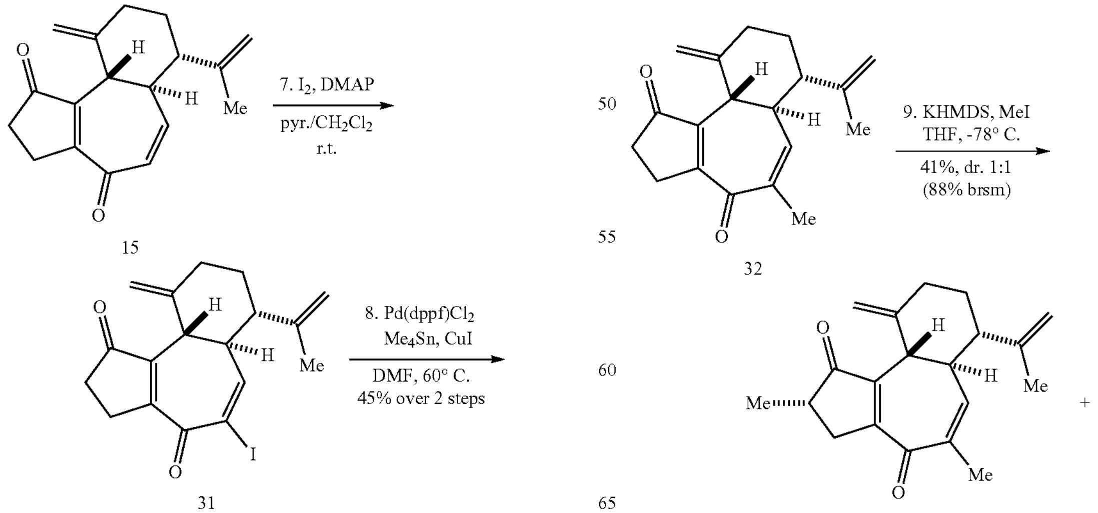

15

31
no purification

32

(-)-Curcusone A (1a)

+

-continued

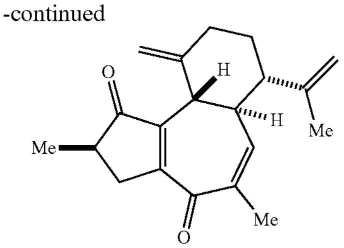

(-)-Curcusone B (1b)

To a solution of 32 (10 mg, 0.036 mmol) in anhydrous THF (2 mL) at −78° C. under an atmosphere of argon was added a solution of KHMDS (1.0 M in THF, 40 μL, 0.04 mmol) dropwise. The mixture was stirred for about 30 min, before adding MeI (8 μL, 0.12). The reaction mixture was stirred for 3 h and then quenched with saturated aqueous $NH_4Cl$ (2 mL). The aqueous layer was extracted with EtOAc (4 mL) and the combined organic layer was washed with brine, dried over $Na_2SO_4$, filtered, and concentrated in vacuo. The crude residue was purified by silica gel column chromatography (5 to 10% EtOAc in hexane) to give (−)-curcusone A (1a, 2.1 mg, 20%), (−)-curcusone B (1b, 2.3 mg, 21%) and recovered compound 32 (5.1 mg, 50%).

(−)-Curcusone A (1a): $^1H$ NMR (500 MHz, $CDCl_3$) δ=5.86 (m, 1H), 4.84 (s, 1H), 4.82 (s, 1H), 4.76 (s, 1H), 4.20 (s, 1H), 3.14 (d, J=12.1 Hz, 1H), 2.82 (ddd, J=18.5, 6.8, 3.1 Hz, 1H), 2.63-2.58 (m, 2H), 2.46-2.41 (m, 2H), 2.35 (ddd, J=12.0, 12.0, 4.2 Hz, 1H), 2.28 (ddd, J=12.8, 12.8, 4.6 Hz, 1H), 1.90-1.86 (m, 1H), 1.83 (dd, J=1.7, 1.7 Hz, 3H); 1.59 (s, 3H), 1.47 (dddd, J=12.8, 12.8, 12.8, 4.7 Hz, 1H), 1.25 (d, J=7.5 Hz, 3H), $^{13}C$ NMR (125 MHz, $CDCl_3$) δ=212.7, 199.1, 160.5, 149.0, 147.7, 147.0, 141.2, 136.4, 113.4, 108.2, 51.9, 45.6, 43.9, 39.2, 36.7, 36.3, 34.6, 19.6, 18.8, 17.8; IR (film): 2923, 2853, 1713, 1660, 1454, 1149 $cm^{-1}$; HRMS (ESI): m/z Calc. for $C_{20}H_{25}O_2$ $[M+H]^+$: 297.1849, found: 297.1850; $[\alpha]_D^{25}$=−311 (c=0.05, $CH_2Cl_2$).

(−)-Curcusone B (1b): $^1H$ NMR (500 MHz, $CDCl_3$) δ=5.87 (m, 1H), 4.82 (dd, J=1.6, 1.6 Hz, 1H), 4.81 (s, 1H), 4.74 (s, 1H), 4.20 (s, 1H), 3.31 (ddd, J=18.4, 7.3, 2.5 Hz, 1H), 3.15 (dt, J=12.3, 3.0 Hz, 1H), 2.59 (m, 1H), 2.49 (ddd, J=7.5, 7.5, 3.4 Hz, 1H), 2.42 (ddd, J=12.5, 4.5, 4.5 Hz, 1H), 2.34 (ddd, J=12.0, 12.0, 4.1 Hz, 1H), 2.27 (ddd, J=12.8, 12.8, 4.5 Hz, 1H), 2.16 (ddd, J=18.5, 3.5, 3.5 Hz, 1H), 1.88-1.85 (m, 1H), 1.84 (dd, J=1.6, 1.6 Hz, 3H), 1.59 (s, 3H), 1.45 (dddd, J=12.8, 12.8, 12.8, 4.6 Hz, 1H), 1.21 (d, J=7.2 Hz, 3H); $^{13}C$ NMR (125 MHz, $CDCl_3$) δ=212.1, 198.5, 158.6, 149.0, 148.8, 147.0, 141.0, 136.7, 113.4, 108.3, 51.9, 46.0, 43.8, 39.8, 36.7, 36.4, 34.6, 19.6, 18.8, 14.7; IR (film): 2955, 2929, 1780, 1715, 1382, 1249, 1093 $cm^{-1}$; HRMS (ESI): m/z Calc. for $C_{20}H_{25}O_2$ $[M+H]^+$: 297.1849, found: 297.1850; $[\alpha]_D^{25}$=−477 (c=0.3, $CH_2Cl_2$).

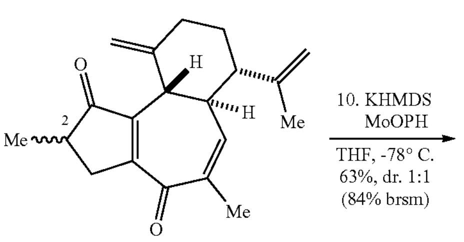

(-)-1a (2S)
(-)-1b (2R)

-continued

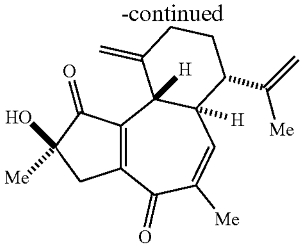

+

(-)-Curcusone C (1c)

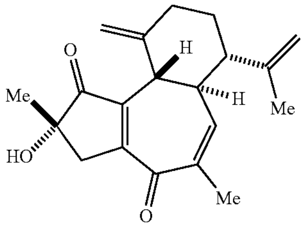

(-)-Curcusone D (1d)

To a solution of a 1:1 mixture 1a and 1b (5 mg, 0.017) in anhydrous THF (2 mL) at −78° C. under an atmosphere of argon, a solution of KHMDS (1.0 M in THF, 20 μL, 0.02 mmol) was added. The reaction mixture was then stirred for 30 min at the same temperature, before adding MoOPH (12 mg, 0.026 mmol). The reaction mixture was stirred at −78° C. for about 2 h before quenching with saturated aqueous $NH_4Cl$ (2 mL). The aqueous phase was extracted with EtOAc (5 mL) and the combined organic layers were washed with brine, dried over $Na_2SO_4$, filtered, and concentrated in vacuo. The crude residue was purified by silica gel column chromatography (10 to 20% EtOAc in hexane) to give (−)-curcusone C (1c, 1.8 mg, 34%), (−)-curcusone D (1d, 1.54 mg, 29%), and a mixture of recovered curcusone A and B (1.2 mg, 24%).

(−)-Curcusone C (1c): $^1H$ NMR (500 MHz, $CDCl_3$) δ=5.86 (m, 1H), 4.85 (dd, J=1.7, 1.7 Hz, 1H), 4.80 (s, 1H), 4.75 (s, 1H), 4.18 (s, 1H), 3.17 (m, 1H), 3.13 (dd, J=18.6, 2.5 Hz, 1H), 2.68 (dd, J=18.3, 3.6 Hz, 1H), 2.66-2.60 (m, 1H), 2.52 (brs, 1H), 2.41 (ddd, J=12.5, 4.4, 2.7 Hz, 1H), 2.35 (ddd, J=11.9, 11.9, 4.2 Hz, 1H), 2.23 (ddd, J=12.5, 12.5, 4.4 Hz, 1H), 1.92-1.87 (m, 1H), 1.85 (dd, J=1.7, 1.7 Hz, 3H), 1.59 (s, 3H), 1.45 (m, 1H), 1.44 (s, 3H); $^{13}C$ NMR (125 MHz, $CDCl_3$) δ=212.3, 198.4, 158.1, 148.7, 146.8, 145.4, 141.2, 136.9, 113.6, 108.3, 74.7, 52.0, 45.4, 43.7, 43.5, 36.7, 34.6, 26.3, 19.6, 18.9; IR (film): 3432, 2924, 2854, 1722, 1648, 1450, 1376, 1052 $cm^{-1}$; HRMS (ESI): m/z Calc. for $C_{20}H_{25}O_3$ $[M+H]^+$: 313.1798, found: 313.1800; $[\alpha]_D^{23}$=−340 (c=0.1, $CH_2Cl_2$).

(−)-Curcusone D (1d): $^1H$ NMR (500 MHz, $CDCl_3$) δ=5.94 (m, 1H), 4.85 (s, 1H), 4.83 (s, 1H), 4.78 (s, 1H), 4.42 (s, 1H), 3.14 (dd, J=12.1, 3.1 Hz, 1H), 3.08 (dd, J=18.2, 3.0 Hz, 1H), 2.66 (dd, J=18.2, 3.0 Hz, 1H), 2.66-2.60 (m, 1H), 2.43 (ddd, J=12.5, 4.7, 3.0 Hz, 1H), 2.34 (ddd, J=11.9, 11.9, 4.3 Hz, 1H), 2.28 (ddd, J=12.4, 12.4, 4.6 Hz, 1H), 2.18 (brs, 1H), 1.91-1.88 (m. 1H), 1.84 (s, 3H), 1.59 (s, 3H), 1.49 (dddd, J=12.5, 12.5, 12.5, 4.8 Hz, 1H), 1.38 (s, 3H); $^{13}C$ NMR (125 MHz, $CDCl_3$) δ=209.3, 197.5, 158.4, 148.3, 146.9, 146.0, 140.9, 137.5, 113.5, 109.1, 73.0, 51.5, 45.6, 43.8, 43.1, 36.4, 34.3, 24.0, 19.7, 18.8; IR (film): 3420, 2926, 2856, 1717, 1648, 1451, 1375, 1054 cm-7; HRMS (ESI): m/z Calc. for $C_{20}H_{25}O_3$ $[M+H]^+$: 313.1798, found: 313.1797; $[\alpha]_D^{23}$=−352 (c=0.1, $CH_2Cl_2$).

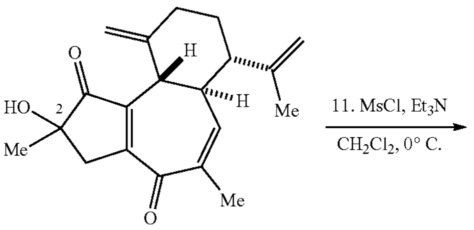

(-)-1c (2R)
(-)-1d (2S)

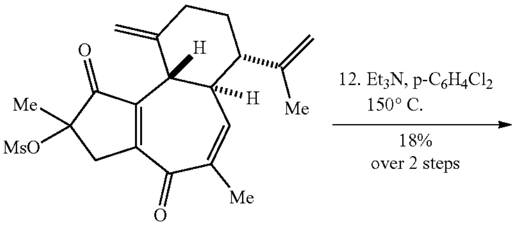

34
no purification

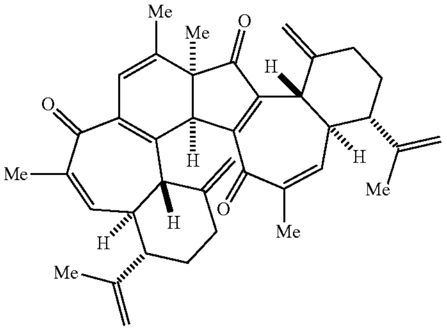

(-)-Dimericursone A (2a)

To a solution of a 1:1 mixture of 1c and 1d (5 mg, 0.016 mmol) in $CH_2Cl_2$ (2 mL) at 0° C. under an atmosphere of argon, was added MsCl (4 µL, 0.05 mmol) and $Et_3N$ (7 µL, 0.05 mmol). The reaction mixture was stirred for about 1 h at the same temperature before quenching with saturated aqueous $NH_4Cl$ (2 mL). The layers were separated, and the aqueous layer was extracted with $CH_2Cl_2$ (5 mL). The combined organic layers were washed with brine, dried over $Na_2SO_4$, filtered, and concentrated in vacuo to give a fairly pure crude product, which was used directly without further purification in the next step.

The above crude product was dissolved in p-dichlorobenzene (2 mL) followed by adding $Et_3N$ (4.5 uL, 0.03 mmol). The mixture was then heated up at 150° C. for 2 h. The reaction mixture was cooled to room temperature and concentrated in vacuo. The crude residue was purified by column chromatography ($SiO_2$, 10% EtOAc in hexane) to give (□)-dimericursone A (2a, 1.25 mg, 18% over two steps) as a yellow solid.

(−)-dimericursone A 2a: $^1H$ NMR (500 MHz, $CDCl_3$) δ=6.17 (s, 1H), 5.72 (brs, 1H), 5.42 (dd, J=5.6, 1.7 Hz, 1H), 4.90 (s, 1H), 4.83 (s, 1H), 4.82 (dd, J=1.5 Hz, 1H), 4.79 (dd, J=1.5 Hz, 1H), 4.76 (s, 1H), 4.74 (s, 1H), 4.66 (s, 1H), 4.10 (s, 1H), 3.83 (d, J=2.8 Hz, 1H), 3.72 (d, J=11.3 Hz, 1H), 2.99 (dd, J=12.0, 2.7 Hz, 1H), 2.55 (ddd, J=11.4, 4.5, 1.9 Hz, 1H), 2.45-2.40 (m, 3H), 2.35-2.25 (m, 4H), 1.91-1.82 (m, 2H), 1.78 (s, 3H), 1.72 (dd, J=1.6, 1.6 Hz, 3H), 1.58 (s, 3H), 1.57 (s, 3H), 1.55 (6H), 1.45 (dq, J=12.8, 4.4 Hz, 2H), 1.25 (s, 3H); $^{13}C$ NMR (125 MHz, $CDCl_3$) δ=207.3, 202.8, 199.2, 162.8, 151.1, 148.6, 147.1, 147.0, 146.8, 144.6, 142.9, 141.1, 135.3, 135.0, 133.8, 130.2, 119.6, 113.2, 113.2, 110.1, 108.2, 59.1, 56.8, 53.7, 51.4, 50.5, 46.0, 44.2, 44.0, 36.5, 36.0, 34.3, 34.3, 20.9, 19.5, 18.8, 18.6, 18.1, 17.9; IR (film): 2926, 2855, 1715, 1679, 1646, 1448, 1375 $cm^{-1}$; HRMS (ESI): m/z Calc. for $C_{39}H_{45}O_3$ $[M+H]^+$: 561.3363, found: 561.3362; $[\alpha]_D^{25}$=−742 (c=0.1, MeOH); reported: $[\alpha]_D^{20}$=−887 (c=0.43, MeOH).

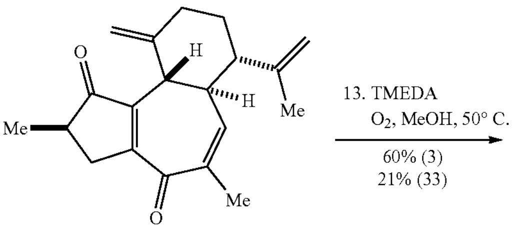

(-)-Curcusone B (1b)

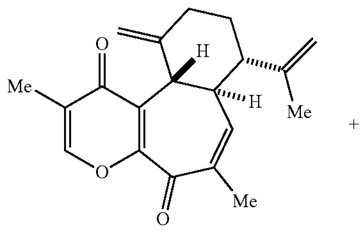

(-)-Pyracurcasone (33)

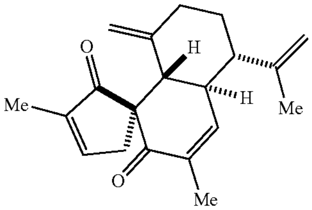

(+)-Spirocurcasone (3)

In a flame dried 8 mL vial, (−)-curcusone B (1b, 20.0 mg, 0.067 mmol) was dissolved in MeOH (3 ml) and the solution was flushed with 02 followed by TMEDA (15.7 mg, 0.13 mmol). The reaction was heated to 50° C. and stirred at this temperature overnight. After the reaction was cooled down, solvent was removed in vacuo. The crude product was purified by preparative TLC (2% EtOAc in hexanes) to obtain (+)-spirocurcasone (3) as white solid (12.0 mg, 60% yield) and (−)-pyracurcasone (33) as white solid (4.5 mg, 21%).

(+)-Spirocurcasone (3): $^1H$ NMR (500 MHz, $CDCl_3$) δ=7.27 (s, 1H), 6.59 (s, 1H), 4.93 (s, 1H), 4.84 (s, 1H), 4.65 (s, 1H), 4.17 (s, 1H), 3.16 (dt, J=18.7, 2.4 Hz, 1H), 3.06 (d, J=10.7 Hz, 1H), 2.46 (ddd, J=18.7, 3.3, 1.9 Hz, 1H), 2.35 (m, 1H), 2.31 (m, 1H), 2.18 (td, J=13.5, 3.9 Hz, 1H), 2.11 (td, J=11.9, 3.7 Hz, 1H), 1.88 (d, J=1.9 Hz, 3H), 1.85-1.81 (m, 1H), 1.73-1.72 (m, 2H), 1.52 (m, 1H); $^{13}C$ NMR (125 MHz, $CDCl_3$) δ=208.7, 199.5, 153.6, 146.8, 146.3, 145.6, 144.2, 133.4, 113.5, 106.9, 60.7, 50.6, 48.1, 41.1, 37.0, 33.8, 33.1, 19.4, 16.2, 10.5; IR (film): 2922, 2854, 1716, 1664, 1643, 1440, 1376, 1330, 1241, 1103, 896 $cm^{-1}$; HRMS (ESI): m/z Calc. for $C_{20}H_{25}NO_2$ $[M+H]^+$: 297.1849, found: 297.1850; $[\alpha]_D^{23}$=+71 (c=0.4, $CHCl_3$).

(−)-Pyracurcamone (33): $^1H$ NMR (500 MHz, $CDCl_3$) δ=7.75 (d, J=1.2 Hz, 1H), 5.84 (dd, J=5.5, 1.7 Hz, 1H), 4.84-4.83 (m, 2H), 4.61 (s, 1H), 4.21 (s, 1H), 3.64 (d, J=12.2

Hz, 1H), 2.58-2.51 (m, 1H), 2.49 (ddd, J=12.6, 4.7, 2.6 Hz, 1H), 2.45-2.36 (m, 2H), 1.94 (d, J=1.2 Hz, 3H), 1.90 (td, J=4.4, 2.5 Hz, 1H), 1.87 (t, J=1.6 Hz, 3H), 1.60 (s, 3H), 1.49 (ddd, J=12.8, 12.8, 4.7 Hz, 1H); $^{13}C$ NMR (125 MHz, $CDCl_3$) δ=193.5, 180.6, 154.9, 151.0, 150.6, 146.9, 140.2, 135.9, 131.4, 125.1, 113.4, 106.2, 51.9, 46.7, 43.0, 36.8, 34.5, 19.1, 18.8, 11.2; IR (film): 2925, 2856, 1683, 1643, 1451, 1333, 1190, 1122, 892 $cm^{-1}$; HRMS (ESI): m/z Calc. for $C_{20}H_{22}NO_3$ $[M+H]^+$: 311.1642, found: 311.1641. $[\alpha]_D^{23}$=−393 (c=0.15, $CHCl_3$).

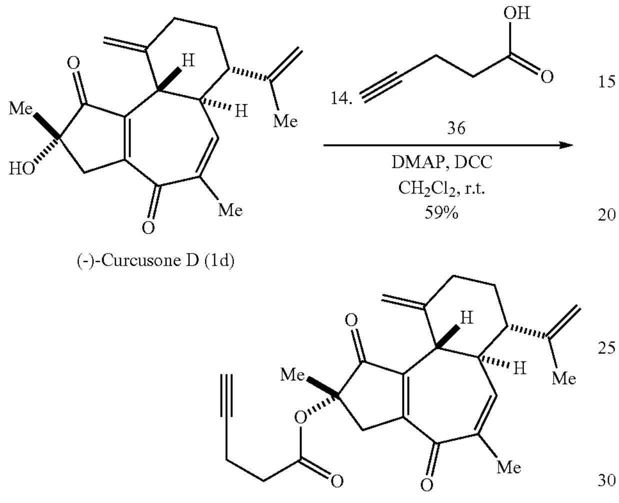

(-)-Curcusone D (1d)

37

(−)-Curcusone D (1d, 8 mg, 0.026 mmol) was dissolved in $CH_2Cl_2$ (0.5 mL) followed by adding pent-4-ynoic acid (3.9 mg, 0.04 mmol) dropwise. After the solution turned to clear, DCC (8.3 mg, 0.04 mmol) was added followed by DMAP (0.6 mg, 0.005 mmol). The reaction was stirred overnight at room temperature. The reaction mixture was quenched with $H_2O$ (2 ML) and the layers were separated. The aqueous layer was extracted with $CH_2Cl_2$ (3 mL) and the combined organic layers were dried over $Na_2SO_4$, filtered and concentrated in vacuo. The crude product was purified by preparative TLC (20% EtOAc in hexane) to obtain probe molecule 37 (6 mg, 59%). $^1H$ NMR (500 MHz, $CDCl_3$) δ=5.97-5.96 (m, 1H), 4.85-4.84 (m, 1H), 4.83-4.82 (m, 3H), 3.38 (dd, J=17.4, 3.4 Hz, 1H), 3.14-3.11 (m, 1H), 2.72-2.66 (m, 1H), 2.63 (dd, J=17.4, 3.4 Hz, 1H), 2.59-2.55 (m, 1H), 2.56 (d, J=6.9 Hz, 1H), 2.49-2.46 (m, 2H), 2.43 (ddd, J=12.7, 5.0, 3.2 Hz, 1H), 2.33 (td, J=11.9, 4.4 Hz, 1H), 2.28-2.22 (m, 1H), 1.98 (t, J=2.6 Hz, 1H), 1.88-1.86 (m, 1H), 1.85 (t, J=1.6 Hz, 3H), 1.59 (s, 3H), 1.52 (dd, J=12.5, 5.0 Hz, 1H), 1.38 (s, 3H); $^{13}C$ NMR (125 MHz, $CDCl_3$) δ=204.8, 197.6, 170.5, 157.4, 147.3, 147.0, 145.6, 140.8, 138.1, 113.5, 110.3, 82.2, 80.0, 69.4, 51.6, 46.3, 43.8, 40.7, 36.3, 34.2, 33.2, 24.1, 19.7, 18.8, 14.4; IR (film): 2923, 2853, 1722, 1661, 1451, 1375, 1272, 1163, 1114, 713 $cm^{-1}$; HRMS (ESI): m/z Calc. for $C_{25}H_{28}O_4$ $[M+H]^-$: 393.2060, found: 393.2059.

Analogs 45-47 are prepared based on the following scheme:

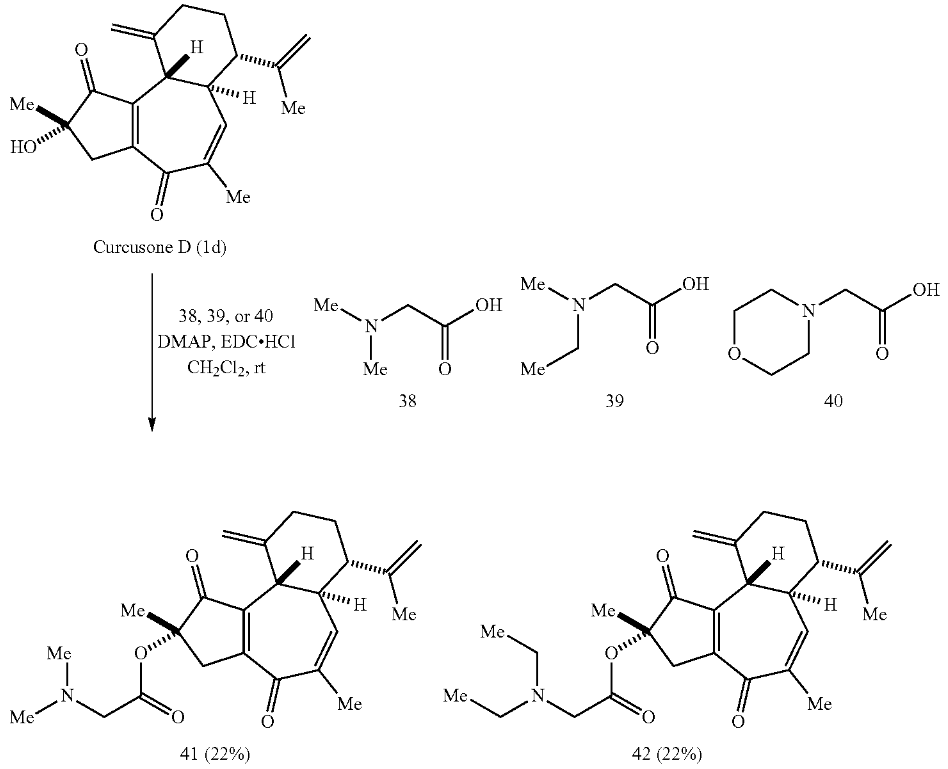

Curcusone D (1d)

38

39

40

41 (22%)

42 (22%)

-continued

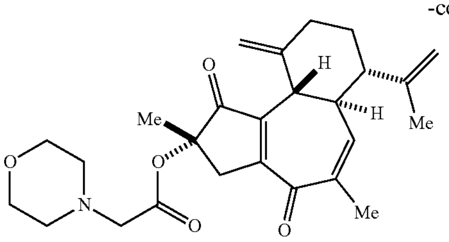

43 (15%)

Analog 41: (−)-Curcusone D (1d, 24.0 mg, 0.077 mmol) was dissolved in $CH_2Cl_2$ (0.8 mL) followed by dimethylglycine (18.0 mg, 0.15 mmol). After the solution was stirred for 5 min, EDC hydrochloride (15.3 mg, 0.08 mmol) was added in one portion followed by DMAP (38 mg, 0.31 mmol). The reaction was stirred overnight at room temperature. The reaction mixture was loaded on and purified by prep TLC (40% EtOAc in hexanes) to obtain product 41 as white solid (6.7 mg, 22% yield). $^1$H NMR (500 MHz, $CDCl_3$) δ=5.99-5.98 (m, 1H), 4.85-4.81 (m, 4H), 3.38 (dd, J=17.3, 3.4 Hz, 1H), 3.23 (d, J=2.5 Hz, 1H), 3.13 (d, J=12.3 Hz, 1H), 2.73-2.67 (m, 1H), 2.65 (dd, J=17.2, 2.5 Hz, 1H), 2.43 (ddd, J=12.6, 5.1, 3.3 Hz, 1H), 2.40-2.30 (s, 6H), 2.28-2.36-2.18 (m, 3H), 1.88-1.83 (m, 1H), 1.85 (t, J=1.6 Hz, 3H), 1.59 (s, 3H), 1.56-1.48 (m, 1H), 1.38 (s, 3H); $^{13}$C NMR (125 MHz, $CDCl_3$) δ=204.7, 197.4, 169.1, 157.4, 147.1, 147.0, 145.6, 140.7, 138.4, 113.5, 110.5, 80.2, 59.9, 51.4, 46.4, 45.2, 43.7, 40.6, 36.2, 34.0, 24.2, 19.7, 18.8; IR (film): 3357, 2923, 2853, 1728, 1663, 1434, 1373, 1243, 1045, 712, 610 $cm^{-1}$; HRMS (ESI): m/z Calc. for $C_{24}H_{31}NO_4$ $[M+H]^+$: 398.2326, found: 398.2326.

Analog 42: (−)-Curcusone D (1d, 16.0 mg, 0.05 mmol) was dissolved in $CH_2Cl_2$ (0.8 mL) followed by diethylglycine (13.1 mg, 0.10 mmol). After the solution was stirred for 5 min, EDC hydrochloride (22.0 mg, 0.11 mmol) was added in one portion followed by DMAP (29 mg, 0.15 mmol). The reaction was stirred overnight at room temperature. The reaction mixture was loaded on and purified by prep TLC (40% EtOAc in hexanes) to obtain product 42 as white solid (9.0 mg, 42% yield). $^1$H NMR (500 MHz, $CDCl_3$) δ=6.00-5.95 (m, 1H), 4.93-4.75 (m, 4H), 3.44-3.30 (m, 3H), 3.16-3.09 (m, 1H), 2.73-2.56 (m, 6H), 2.43 (ddd, J=12.6, 5.1, 3.3 Hz, 1H), 2.32 (td, J=11.8, 4.5 Hz, 1H), 2.28-2.20 (m, 1H), 1.90-1.76 (m, 1H), 1.85 (t, J=1.6 Hz, 3H), 1.59 (t, J=1.0 Hz, 3H), 1.57-1.44 (m, 1H), 1.37 (s, 3H), 1.05 (t, J=7.1 Hz, 6H); $^{13}$C NMR (125 MHz, $CDCl_3$) δ=204.8, 197.5, 170.2, 157.3, 147.1, 145.7, 140.7, 138.3, 113.5, 110.6, 79.9, 53.8, 51.5, 48.0, 46.4, 43.7, 40.6, 36.2, 34.1, 24.2, 19.7, 18.8, 12.4 (Missing one sp2 carbon); IR (film): 2923, 2853, 1724, 1650, 1434, 1374, 1243, 1097, 1046, 712, 612 $cm^{-1}$; HRMS (ESI): m/z Calc. for $C_{26}H_{35}NO_4$ $[M+H]^-$: 426.2639, found: 426.2638.

Analog 43: (−)-Curcusone D (1d, 16.0 mg, 0.05 mmol) was dissolved in $CH_2Cl_2$ (0.8 mL) followed by morpholin-4-yl-acetic acid hydrochloride (18.0 mg, 0.10 mmol). After the solution was stirred for 5 min, EDC hydrochloride (19.0 mg, 0.10 mmol) was added in one portion followed by DMAP (31 mg, 0.25 mmol). The reaction was stirred overnight at room temperature. The reaction mixture was loaded on and purified by prep TLC (40% EtOAc in hexanes) to obtain product 43 as white solid (6.7 mg, 15% yield). $^1$H NMR (500 MHz, $CDCl_3$) δ=6.06-5.90 (m, 1H), 4.84 (t, J=1.7 Hz, 1H), 4.83-4.81 (m, 3H), 3.74 (t, J=4.7 Hz, 4H), 3.37 (dd, J=17.4, 3.4 Hz, 1H), 3.26 (s, 2H), 3.17-3.10 (m, 1H), 2.73-2.65 (m, 1H), 2.66 (dd, J=17.3, 2.5 Hz, 1H), 2.59 (d, J=4.9 Hz, 4H), 2.43 (ddd, J=12.6, 5.1, 3.3 Hz, 1H), 2.32 (td, J=11.9, 4.5 Hz, 1H), 2.29-2.20 (m, 1H), 1.91-1.79 (m, 1H), 1.85 (t, J=1.7 Hz, 3H), 1.59 (d, J=1.2 Hz, 3H), 1.57-1.47 (m, 1H), 1.38 (s, 3H); $^{13}$C NMR (125 MHz, $CDCl_3$) δ=204.6, 197.3, 168.8, 157.4, 147.2, 147.0, 145.6, 140.6, 138.4, 113.5, 110.5, 80.3, 66.8, 59.3, 53.2, 51.4, 46.4, 43.7, 40.6, 36.1, 34.0, 24.1, 19.7, 18.8; IR (film): 2923, 2853, 1720, 1660, 1452, 1375, 1273, 1113, 1026, 712 $cm^{-1}$; HRMS (ESI): m/z Calc. for $C_{26}H_{33}NO_5$ $[M+H]^-$: 440.2431, found: 440.2431.

Biological Methods

Cell Culture and Preparation of Lysates

HeLa, MCF-7, and MDA-MB-231 cells were maintained in DMEM (Corning MT10013CV) supplemented with 10% fetal calf serum (FCS, Gibco 10437028), Ix MEM non-essential amino acids solution (100× Gibco 11140050), and 1× penicillin-streptomycin (pen-strep, 100× Sigma-Aldrich P4333). Cells were grown at 37° C. under 5% $CO_2$ atmosphere. Cells were grown to confluence and were harvested by scraping, centrifuging at 1,500×g for five min at 4° C. and resuspending in PBS. Cells were lysed by sonication to form cell lysates, and protein concentration was determined using the Bradford assay (Biorad) unless noted otherwise and measured using a BioTek Synergy H1 microplate reader.

Cytotoxicity of Curcusones in Various Cell Lines

MCF-7 (3e4) cells were seeded in a 96-well plate. After incubating overnight, the cells were treated with the indicated compound (1:1000 from a DMSO stock), DMSO (0.1% final), or 10% v/v DMSO as a positive control in DMEM with FCS. After 24 hours, the cells were imaged (Olympus IX51 inverted microscope) and then treated with 5% v/v WST1 (Sigma-Aldrich) incubated at 37° C. for 1 hour. The absorbance at 420 nm and 630 nm was then acquired using a BioTek Synergy H1 microplate reader. Cell viability results were plotted in GraphPad Prism 7.

In Situ Competitive MS-Based Target Identification

MCF-7 (8e6) cells were seeded in 10 cm Petri dishes and incubated overnight. Cells were washed once with DPBS the following day and treated with either DMSO or 30 μM 1d (1:1000 from DMSO stock) for 4 hours in DMEM without FCS at 37° C. Lysate was prepared as described above. Lysate (2 mg/mL, 0.75 mL) was treated with 10 μM 37 (50× stock in DMSO) for one hour at r.t. and then subjected to click chemistry. Biotin alkyne (Click Chemistry Tools, 50 μM, 50× stock in DMSO), tris(2-carboxyethyl)phosphine hydrochloride (TCEP) (1 mM, Sigma-Aldrich C4706-2G, 50× fresh stock in water), tris[(1-benzyl-1H1,2,3-triazol-4-yl)methyl]amine (TBTA) (100 μM, Click Chemistry Tools, 16× stock in DMSO:tBuOH 1:4), and copper(II) sulfate (Sigma-Aldrich, 1 mM, 50× stock in water) were added to the proteome and left to react for one hour at r.t. Protein was precipitated by adding MeOH (4 vol.), $CHCl_3$ (1 vol.), and water (3 vol.) to the reaction mixture and the turbid mixture was centrifuged for five min at 20,000×g at 4° C. yielding a protein layer between the aqueous and organic layers. The protein layer was isolated, dried, and solubilized in 2% SDS in PBS via sonication. Tube was centrifuged at 4,700×g for five min, and the soluble fraction was transferred to a new tube. PBS was added to give a final SDS concentration of 0.2%. 160 μL of streptavidin agarose beads (ProteoChem) were added and the mixture was rotated for four hours at r.t. Beads were washed with 1% SDS in PBS (1×10 mL), PBS (3×10 mL), and water (3×10 mL). Beads were resuspended in 6 M urea in PBS (500 μL), reduced with 10 mM neutralized TCEP (20× fresh stock in water) for 30 min at r.t., and alkylated with 25 mM iodoacetamide (400 mM fresh stock in water) for 30 min at r.t. in the dark. Beads were pelleted by centrifugation (1,400×g, two min) and resuspended in 150 μL of 2 M urea, 1 mM $CaCl_2$ (100× stock in water) and trypsin (Thermo Scientific, 1.5 μL of 0.5 μg/μL) in 50 mM $NH_4HCO_3$. The digestion was performed for 6 hours at 37° C. Samples were acidified to a final concentration of 5% acetic acid, desalted over a self-packed C18 spin column, and dried. Samples were analyzed by LC-MS/MS (see below) and the MS data was processed with MaxQuant (see below).

LC-MS/MS Analysis

Peptides were resuspended in water with 0.1% formic acid (FA) and analyzed using EASY-nLC 1200 nano-UHPLC coupled to Q Exactive HF-X Quadrupole-Orbitrap mass spectrometer (Thermo Scientific). The chromatography column consisted of a 50 cm long, 75 μm i.d. microcapillary capped by a 5 μm tip and packed with ReproSil-Pur 120 C18-AQ 2.4 μm beads (Dr. Maisch GmbH). LC solvents were 0.1% FA in $H_2O$ (Buffer A) and 0.1% FA in 90% MeCN: 10% $H_2O$ (Buffer B). Peptides were eluted into the mass spectrometer at a flow rate of 300 nL/min over a 240 min linear gradient (5-35% Buffer B) at 65° C. Data was acquired in data-dependent mode (top-20, NCE 28, R=7, 500) after S25 full MS scan (R=60,000, m/z 400-1,300). Dynamic exclusion was set to 10 s, peptide match to prefer and isotope exclusion was enabled.

MaxQuant Analysis

The MS data was analyzed with MaxQuant9 (V1.6.1.0)[7] and searched against the human proteome (Uniprot) and a common list of contaminants (included in MaxQuant). The first peptide search tolerance was set at 20 ppm, 10 ppm was used for the main peptide search and fragment mass tolerance was set to 0.02 Da. The false discovery rate for peptides, proteins and sites identification was set to 1%. The minimum peptide length was set to 6 amino acids and peptide re-quantification, label-free quantification (MaxLFQ) and "match between runs" were enabled. The minimal number of peptides per protein was set to two. Methionine oxidation was searched as a variable modification and carbamidomethylation of cysteines was searched as a fixed modification.

Overexpression of FLAG-BRAT1 in HEK-293T

HEK-293T (8e6) cells were seeded in a 10 cm dish in DMEM without pen-strep. After incubating overnight, 24 μg of FLAG-BRAT1 pExp plasmid was incubated for 15 min at r.t. with 96 μL of PEI MAX™ 40K (Polysciences 24765-1) in final volume of 2 mL Opti-MEM (Gibco 11058021). The mixture was then carefully added to the cells. After 24 hours, the cells were carefully washed twice with PBS, and the lysate was prepared by sonication in PBS as described above.

Thermal Shift Assay of FLAG-BRAT1 Via Western Blotting.

The overexpressed FLAG-BRAT1 lysate (2 mg/mL) was treated with DMSO or 1d (30 μM from a 25× stock in DMSO) for 1 h at r.t., heated for 3 minutes at the indicated temperature (34° C. to 61° C.), cooled at r.t. for 3 min, and then chilled on ice for 3 min before centrifugation for 20 min at 17,000×g at 4° C. The supernatant was carefully isolated. SDS-PAGE reducing loading buffer (4×) was added to the isolated supernatant, and proteins were transferred to a PVDF (0.2 μm) membrane using wet transfer with tris-glycine transfer buffer (20% methanol) for one hour at 350 mA. Membrane was blocked with 5% milk in tris-buffered saline with 0.1% Tween 20 (TBST) for 30-60 minutes at r.t. and then incubated with primary rabbit polyclonal BRAT1 antibody (Novus NB100-2256, 1:2000 in 5% milk in TBST) overnight shaking at 4° C. Membrane was washed three times for five min with TBST and incubated with anti-rabbit Alexa Fluor 647 (Jackson ImmunoResearch Inc., 1:500 in 5% milk in TBST) for one hour at r.t. Membrane was then washed 3× with TBST and visualized with an Azure Biosystems Sapphire Biomolecular Imager. Membrane was then washed with TBST and incubated with mouse monoclonal p-tubulin antibody (Proteintech 66240-1-Ig; 1:10,000 in 5% milk in TBST) for 2 hours at r.t. or overnight at 4° C. Membrane was washed, incubated with anti-mouse Alexa Fluor 488 (Jackson ImmunoResearch Inc., 1:500 in 5% milk in TBST), and scanned as described above.

In Situ Competitive Pulldown Assay Via Western Blotting

MCF-7 (8e6) and HeLa (4e6) cells were seeded in 10 cm dishes, and MDA-MB-231 (14e6) cells were seeded in 15 cm dishes. After incubating overnight, the cells were washed once with DPBS and treated with 10 μM 1d (1:1000 from DMSO stock) or DMSO (0.1% final) for 4 hours in DMEM without FCS. The lysates were prepared and quantified as described above. Lysates (2 mg/ml, 0.5 mL) was treated with 10 μM 37 (50× stock in DMSO) or DMSO for one hour at r.t. and then subjected to click chemistry with biotin azide as described above for one hour at r.t. Protein was precipitated using MeOH (4 vol.), $CHCl_3$ (1 vol.) and water (3 vol.) as described above. The protein layer was isolated, dried, and solubilized in 0.2% SDS in PBS (1 mL) via sonication; 70 μL of streptavidin agarose beads (ProteoChem) were added and the mixture was rotated overnight at r.t. in the dark. Beads were washed with 1% SDS in PBS (2×1 mL), 6 M urea in PBS (2×1 mL), and PBS (3×1 mL). Beads were pelleted by centrifugation (1,400×g, two min), and the supernatant was carefully removed. Enriched proteins were eluted from the beads with 35 μL SDS-PAGE reducing loading buffer (4×), then were subjected to 10 min heat denaturation (95° C.), and were separated using a 11% SDS-PAGE gel. Western blotting was performed as described above, β-Tubulin was used as a loading control, because it was detected but not competed by 1d in the competitive MS-based target identification (LFQ ratio of TUBB6 was 1.02±0.17).

In Situ Dose Response and Kinetics Via Competitive Pulldown Assay

HeLa (2.0e6) cells were seeded in 60 mm dishes. After incubating overnight, cells were washed with DPBS and treated with 1, 3, 10, or 30 μM 1d (1:1000 from DMSO stock) or DMSO (0.1% final) in DMEM without FCS for 1, 2, or 4 hours at 37° C. The lysates were prepared and quantified as described above. Lysates (2 mg/mL, 140 μL) was treated with 10 μM 37 (50× stock in DMSO) for one hour at r.t. and then subjected to click chemistry with biotin azide as described above for one hour at r.t. Proteins were precipitated, re-solubilized in 0.2% SDS in PBS, enriched with 50 μL streptavidin beads, and washed as described above. Proteins were eluted using 30 μL SDS-PAGE reducing loading buffer (4×), subjected to 10 min heat denaturation (95° C.), separated using a 11% SDS-PAGE gel, and visualized via Western blotting as described above. Images were quantified with ImageJ. $EC_{50}$ and Kitz-Wilson binding constants were calculated using GraphPad Prism 7.

Generation of BRAT1 shRNA Knockdown Cell Lines

BRAT1 retroviral shRNA and non-targeting control plasmids (transOMIC) were supplied by the Genetic Perturbation Screening facility at The Scripps Research Institute. HEK-293T (4e6) cells were seeded in a 10 cm plate in 10 mL of DMEM without pen-strep. At ~70% confluency, the cells were subjected to transfection with 10 μg each of BRAT1 shRNA or non-targeting control plasmid and pCL-ECO plasmid (Addgene 12371) with 80 μL of PEIMAX-40 (Polysciences 24765-1) with a final volume of 950 μL in Opti-MEM (Gibco 11058021) after the transfection reagents incubated together for 15 min at r.t. After 6-8 hours of transfection, the media was replaced with 8 mL of DMEM without pen-strep. The supernatant was collected at 48 and 72 hours, filtered through a 0.45 μm syringe filter, and combined. HeLa cells (0.2e6) in a 6-well dish were incubated overnight and then subjected to retroviral transduction with gentle and slow centrifugation. After 24 hours, cells were selected with 2 μg/mL puromycin for 2 weeks, and BRAT1 knockdown was monitored by Western blotting as described above.

Global Proteomics Profiling Using LC-MS/MS

For 1d compound treatment, HeLa (0.8e6) cells were seeded in 6-well plates. After incubating overnight, the cells were treated with 3 μM 1d (1:1000 from DMSO stock) or DMSO (0.1% final) for 24 hours in DMEM media with 10% FCS. For BRAT1 knockdown, the BRAT1 knockdown or non-targeting control (WT) HeLa cells were grown to full confluency over 24 hours. Lysates were prepared and quantified as described above. The lysates (2 mg/mL; 15 μL in PBS per replicate) were brought up to a final concentration of 6 M urea using fresh 9 M urea in 100 mM $NH_4HCO_3$ and then were incubated with 10 mM TCEP for 30 min at r.t. while rotating. For alkylation, 25 mM IAA was added and incubated for 30 min at r.t. under rotation in the dark. Solution was diluted to 2 M urea with 50 mM $NH_4HCO_3$ and 1 mM $CaCl_2$, and then 1.5 μg trypsin (Thermo Scientific) was added. Tryptic digestion was performed overnight at 37° C. Peptides were desalted over a self-packed C18 spin column and dried. Samples were analyzed by LC-MS/MS (see above) and the MS data was processed with MaxQuant (see above) and analyzed in Perseus. BRAT1 expression following 1d (3 μM) treatment of HeLa cells for 24 hours was measured via Western blot as described above.

Transwell Migration Assay

For compound treatment, MCF-7 (1e5), HeLa (5e4), or MDA-MB-231 (3e4) cells were seeded in a transwell migration chamber (Greiner Bio-One 07-000-396) in DMEM without FCS (final volume 200 μL) but with 1 μM 1d (1:1000 from DMSO stock) or DMSO (0.1% final). DMEM with FCS (final volume 700 μL) containing 1 μM 1d (1:1000 from DMSO stock) or DMSO (0.1% final) was placed in the lower chamber. For knockdown genetic control, BRAT1 knockdown or non-targeting control HeLa (54) cells were seeded in a transwell migration chamber in DMEM without FCS (final volume 200 μL); DMEM with FCS (final volume 700 μL) was placed in the lower chamber. After 24 hours of incubation, the media was carefully removed, and the cells were fixed with 100% MeOH for 10 minutes and then stained with 0.5% w/v crystal violet (20% MeOH in $H_2O$) for 10 minutes. Cells inside the chamber were physically removed and then the migrated cells were imaged (Olympus IX51 inverted microscope), counted with ImageJ, and plotted in GraphPad Prism 7.

Visualization of DNA Double Strand Breaks Via γH2AX Fluorescence Microscopy

BRAT1 knockdown (1e5) or non-targeting control (7e4) HeLa cells were seeded in a 24-well plate containing a coverslip. After incubating overnight, the cells were treated with 3 μM 1d (1:1000 from DMSO stock), 30 μM etoposide, 3 μM 1d combined with 30 μM etoposide, or DMSO (0.2% final) for 24 hours in DMEM with FCS. Cells were washed one time with PBS and fixed with methanol at −20° C. for 10 min. Cells were washed again two times with PBS, and the coverslip was transferred to a wet box. Blocking was performed with a 5% bovine serum albumin (BSA) solution in PBS for 30 min. Cells were washed one time with 0.1% BSA in PBS, and rabbit antibody directed against H2AX pS139 (Sigma Aldrich H5912, 1:400 in PBS 0.1% BSA) was added and incubated for one hour at r.t. Cells were washed three times with PBS 0.1% BSA and incubated for one hour with anti-rabbit IgG Alexa Fluor 488 (Jackson, 1:200 in PBS 0.1% BSA). Cells were washed three times with PBS 0.1% BSA, one time with PBS, one time with water and then mounted on a slide with ProLong Gold antifade mountant with DAPI (Life Technologies). Cells were visualized with an BX53 fluorescent microscope (Olympus). Intensity of >50 cells were measured per replicate using ImageJ.

Synergistic Toxicity with Etoposide

For compound treatment, HeLa (1e4), MCF-7 (3e4), or MDA-MB-231 (1.5e4) cells were seeded in a 96-well plate and left to attach overnight. Cells were treated with DMSO (0.2% final), 1d (1 or 3 M as indicated), etoposide (50 μM), or both 1d (1 or 3 μM as indicated) and etoposide (50 IM) combined (compounds diluted from 1:1000 DMSO stocks). For knockdown genetic control, BRAT1 knockdown or non-targeting control HeLa (1e4) cells were seeded. After incubating overnight, the cells were treated with DMSO (0.1% final) or 50 μM etoposide (1:1000 DMSO stock). After 24 hours, the cells were imaged, treated with 5% v/v WST1, and quantified as described above.

In one embodiment, the present disclosure provides a compound of formula I:

I

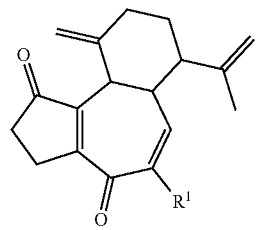

or any stereoisomer, wherein $R^1$ is H, F, Cl, Br, I, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof.

In one embodiment regarding to the compound of formula I, wherein $R^1$ is H, I or methyl.

In one embodiment regarding to the compound of formula I, wherein the compound of formula I is a chiral compound of Formula II:

II

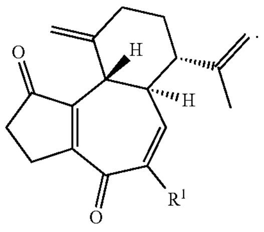

In one embodiment, the present disclosure provides a compound of Formula III:

III

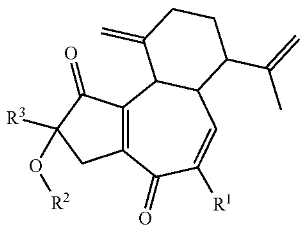

or any pharmaceutically acceptable salt thereof, wherein $R^1$ and $R^3$ are each independently CN, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, $R^2$ is H, —($SO_2$)—$R^7$, or —(C═O)—$R^7$, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^7$ is an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^7$ is $NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S, provided that the compound is not:

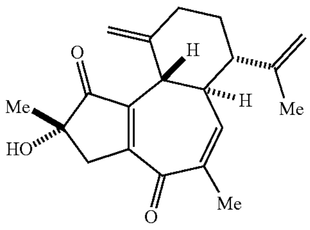

or any stereoisomer thereof.

In one embodiment regarding the compound of Formula al, wherein $R^2$ is —(C═O)—$CH_2$—$NR^8R^9$, wherein $R^8$ and $R^9$ are each independently H, an optionally substituted $C_1$-$C_6$ straight or branched alkyl group, or an optionally substituted $C_3$—C carbon ring wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

In one embodiment regarding the compound of Formula III, wherein the compound is a compound of Formula IV:

IV

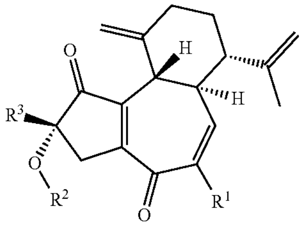

or any pharmaceutically acceptable salt thereof

In one embodiment regarding the compound of Formula III or Formula IV, wherein the compound is selected from the group consisting of:

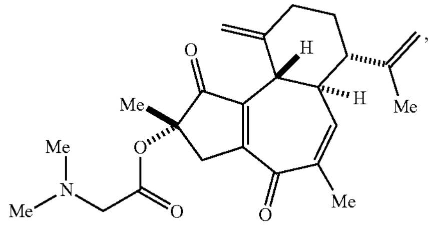

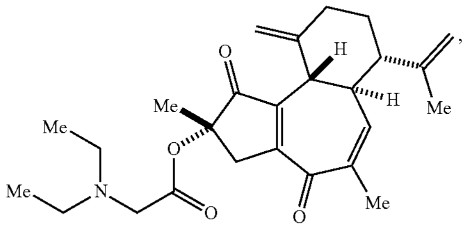

-continued

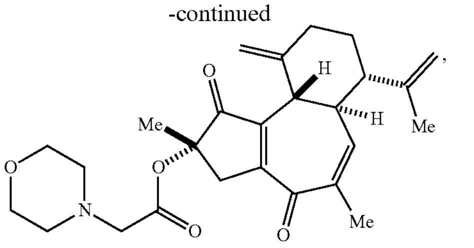

and any pharmaceutically acceptable salt thereof.

In one embodiment, the present disclosure provides a synthetic method to prepare a curcusone compound D or an isomer thereof, wherein the method comprises:

providing a compound of Formula A and treating the compound of Formula A under a halogenation condition to provide a compound of Formula B;

treating the compound of Formula B under a first methylation condition to provide a compound of Formula C, or any isomer thereof; and treating the compound of Formula C under a second methylation condition to provide a compound of Formula D or an isomer thereof, wherein X is Cl, Br, or I.

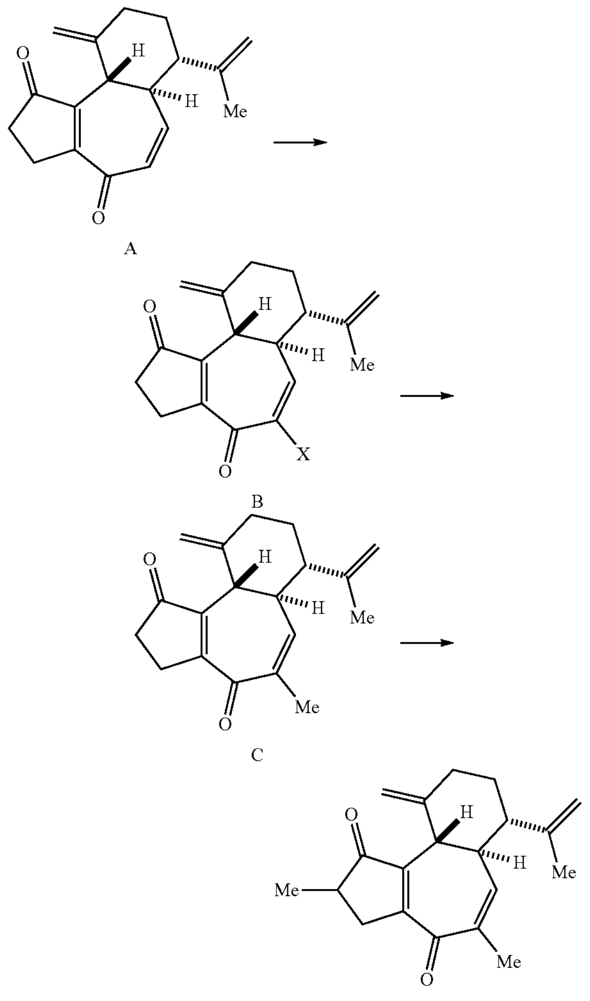

A

B

C

D

In one aspect regarding the synthetic method to prepare the curcusone compound D or an isomer thereof, wherein X is I.

In one embodiment, the present disclosure provides a method of using a compound of Formula III as a BRCA1-associated ATM activator 1 (BRAT1) inhibitor, wherein the compound of Formula III is:

III

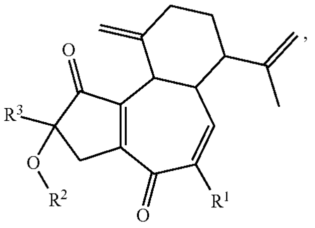

or any stereoisomer, any pharmaceutically acceptable salt thereof, wherein $R^1$ and $R^3$ are each independently CN, $CO_2R^4$, $CONR^4R^5$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, $R^2$ is H, —$(SO_2)$—$R^7$, or —(C═O)—$R^7$, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^7$ is an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^7$ is $NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

In one embodiment regarding the method of using a compound of Formula III as a BRCA1-associated ATM activator 1 (BRAT1) inhibitor, wherein the compound has a Formula IV:

IV

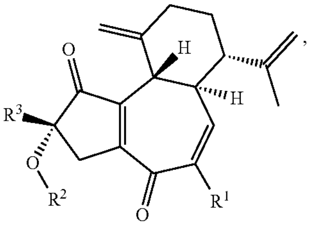

or any pharmaceutically acceptable salt thereof, wherein $R^1$-$R^3$ are the same as defined in Formula I.

In one embodiment regarding the method of using a compound of Formula III as a BRCA1-associated ATM activator 1 (BRAT1) inhibitor, wherein $R^2$ is —(C═O)—$CH_2$—$NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

In one embodiment regarding the method of using a compound of Formula III as a BRCA1-associated ATM activator 1 (BRAT1) inhibitor, wherein the compound is selected from the group consisting of:

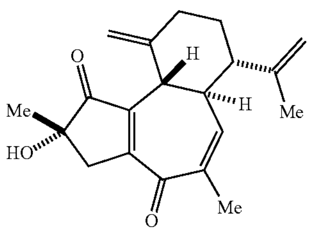
,

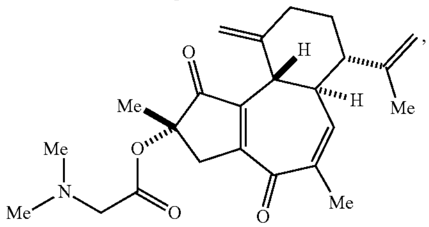
,

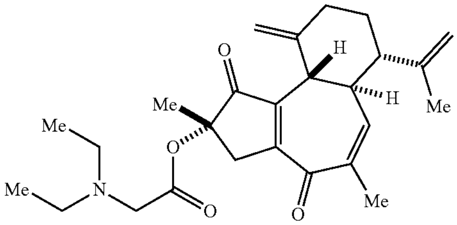
,

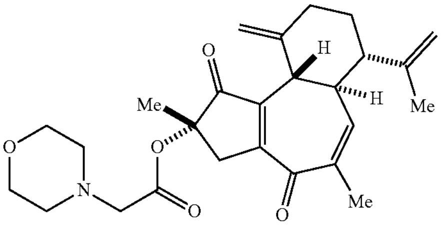
, and any pharmaceutically acceptable salt thereof.

Those skilled in the art will recognize that numerous modifications can be made to the specific implementations described above. The implementations should not be limited to the particular limitations described. Other implementations may be possible.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

We claim:

1. A compound of Formula I:

I

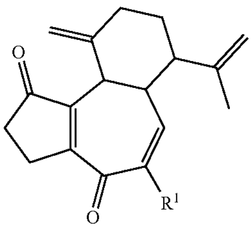

or any stereoisomer, or a pharmaceutically acceptable salt thereof, wherein $R^1$ is H, F, Cl, Br, I, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof.

2. The compound of claim 1, wherein the compound has a Formula II:

II

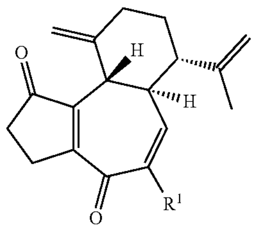
.

3. The compound of claim 1, wherein $R^1$ is H, I or methyl.

4. A method of using a compound of Formula III as a BRCA1-associated ATM activator 1 (BRAT1) inhibitor to treat cancer in a subject, the method comprising administering a compound of Formula III to the subject, wherein the compound of Formula III is:

III

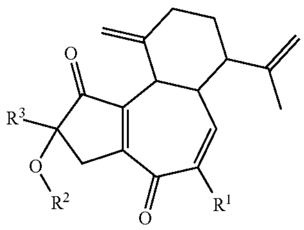
, or any stereoisomer, any pharmaceutically acceptable salt thereof, wherein $R^1$ and $R^3$ are each independently CN, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, $R^2$ is H, —$(SO_2)$—$R^7$, or —(C═O)—$R^7$, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^7$ is an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^7$ is $NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

5. The method of claim 4, wherein the compound has a Formula IV:

IV

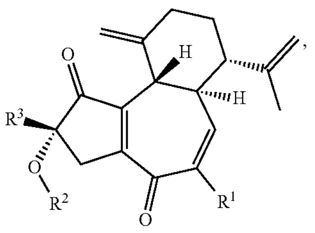

or any pharmaceutical acceptable salt thereof.

6. The method of claim 4, wherein $R^2$ is —(C═O)—$CH_2$—$NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

7. The method of claim 4, wherein the compound is selected from the group consisting of:

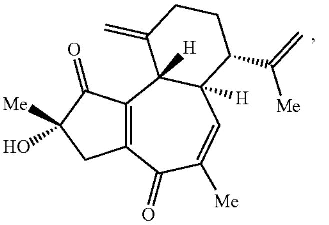

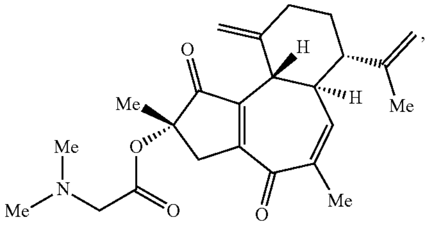

-continued

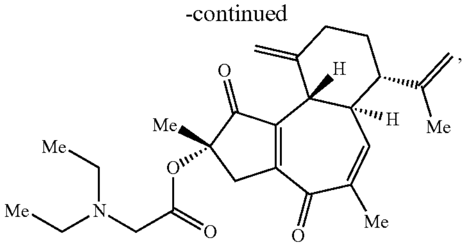

or

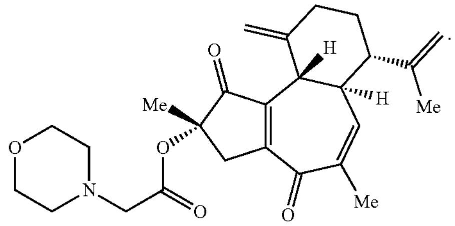

8. A compound of Formula III:

III

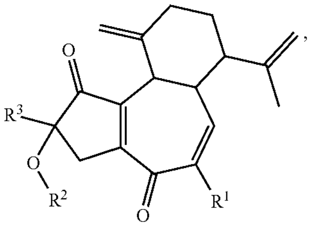

or a pharmaceutically acceptable salt thereof, wherein $R^1$ and $R^3$ are each independently CN, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, $R^2$ is H, —$(SO_2)$—$R^7$, or —(C═O)—$R^7$, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^7$ is an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^7$ is $NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S, provided that the compound is not:

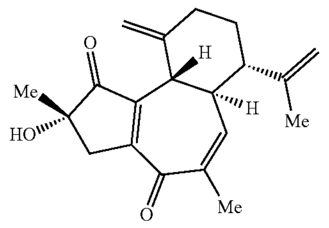

or any stereoisomer thereof.

9. The compound of claim 8, wherein $R^2$ is —(C═O)—$CH_2$—$NR^8R^9$, wherein $R^8$ and $R^9$ are each independently H, an optionally substituted $C_1$-$C_6$ straight or branched alkyl group, or an optionally substituted $C_3$-$C_6$ carbon ring wherein 1 or 2 carbon of the $C_3$-$C_6$ carbon ring can be replaced by N, O, or a combination thereof, or RR and $R^9$ can jointly form an nitrogen-containing 3-8 membered ring, wherein the ring can have 1-3 hetero atom selected from the group consisting of O, N, and S.

10. The compound of claim 8, wherein the compound is a compound of Formula IV:

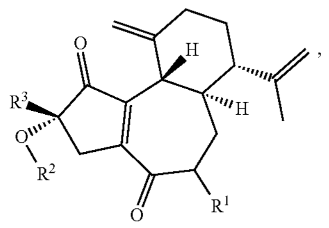

IV or any pharmaceutically acceptable salt thereof.

11. The compound of claim 8, wherein the compound is selected from the group consisting of:

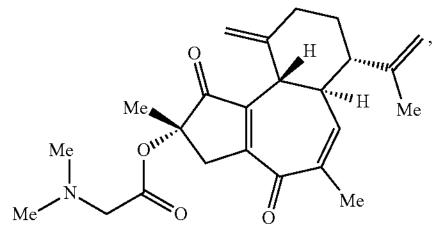

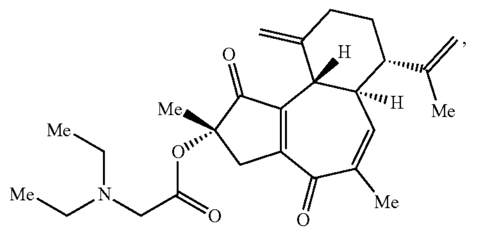

-continued

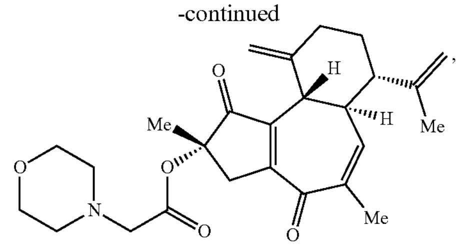

and any pharmaceutically acceptable salt thereof.

12. A synthetic method to prepare a curcusone compound D or an isomer thereof, comprising:

providing a compound of Formula A and treating the compound of Formula A under a halogenation condition to provide a compound of Formula B;

treating the compound of Formula B under a first methylation condition to provide a compound of Formula C, or any isomer thereof; and treating the compound of Formula C under a second methylation condition to provide a compound of Formula D or an isomer thereof, wherein X is Cl, Br, or I.

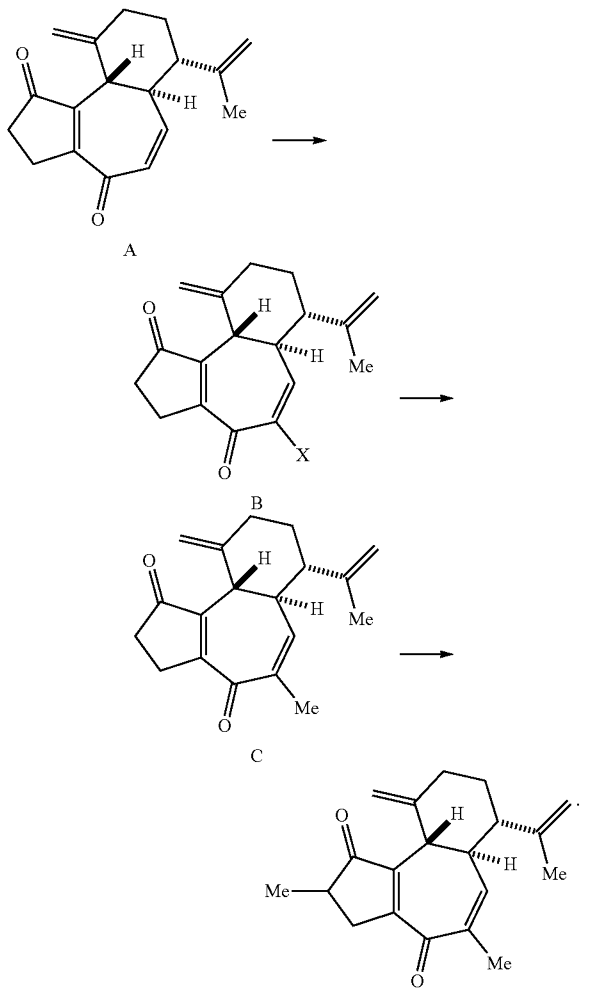

A

B

C

D

13. The method of claim 12, wherein X is I.

14. A method of inducing cytotoxicity in cancer cells, the method comprising treating cancer cells with a compound of Formula III, wherein the compound of Formula III is:

III

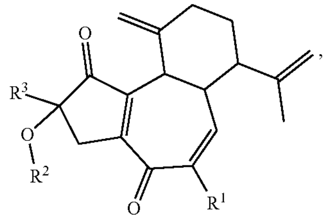

or any stereoisomer, any pharmaceutically acceptable salt thereof, wherein $R^1$ and $R^3$ are each independently CN, $CO_2R^4$, $CONR^5R^6$, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, $R^2$ is H, —$(SO_2)$—$R^7$, or —(C═O)—$R^7$, wherein $R^4$, $R^5$, and $R^6$ are each independently H, or an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, wherein $R^7$ is an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^7$ is $NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

15. The method of claim 14, wherein the compound has a Formula IV:

IV

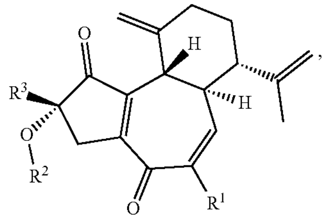

or any pharmaceutical acceptable salt thereof.

16. The method of claim 14, wherein $R^2$ is —(C═O)—$CH_2$—$NR^8R^9$, wherein $R^8$ and $R^9$ are each independently H, an optionally substituted $C_1$-$C_6$ straight or branched alkyl group, or an optionally substituted $C_3$-$C_6$ carbon ring, wherein 1 or 2 carbon of the $C_3$-$C_6$ carbon ring can be replaced by N, O, or a combination thereof, or $R^8$ and $R^9$ can jointly form an nitrogen-containing 3-8 membered ring, wherein the ring can have 1-3 hetero atom selected from the group consisting of O, N, and S.

17. The method of claim 14, wherein the compound is selected from the group consisting of:

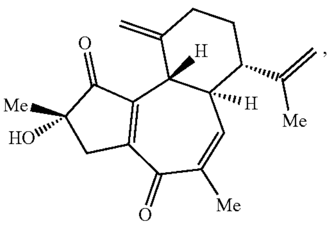

,

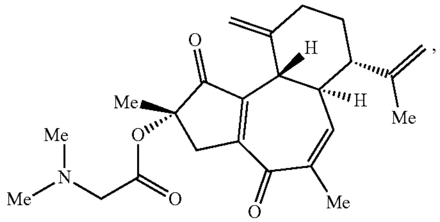

,

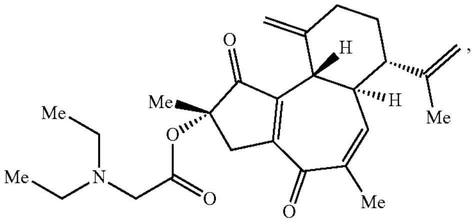

, or

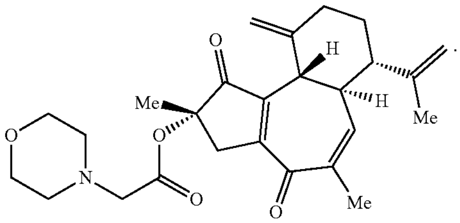

.

* * * * *